United States Patent [19]

Böshagen et al.

[11] Patent Number: 4,465,684

[45] Date of Patent: Aug. 14, 1984

[54] 3,4,5-TRIHYDROXYPIPERIDINE COMPOUNDS AND THEIR USE AS MEDICAMENTS AND IN ANIMAL NUTRITION

[75] Inventors: Horst Böshagen, Haan; Bodo Junge, Wuppertal; Jürgen Stoltefuss, Haan; Delf Schmidt, Wuppertal; Hans P. Krause, Wuppertal; Walter Puls, Wuppertal, all of Fed. Rep. of Germany

[73] Assignee: Bayer Aktiengesellschaft, Leverkusen, Fed. Rep. of Germany

[21] Appl. No.: 323,153

[22] Filed: Nov. 20, 1981

Related U.S. Application Data

[63] Continuation of Ser. No. 153,286, May 27, 1980, abandoned.

[30] Foreign Application Priority Data

Jun. 5, 1979 [DE] Fed. Rep. of Germany ....... 2922760

[51] Int. Cl.³ .................. A61K 31/445; C07D 401/12; C07D 401/14

[52] U.S. Cl. .................. 424/250; 424/267; 544/364; 546/188; 546/187

[58] Field of Search ............... 542/413, 417, 418, 421, 542/423, 427, 437, 447, 476, 435, 436, 414; 544/364; 546/187, 188; 424/267, 250

[56] References Cited

U.S. PATENT DOCUMENTS 4,336,373  6/1982  Matsumura et al. ................ 542/447

FOREIGN PATENT DOCUMENTS 2067989  8/1981  United Kingdom ................ 542/447

*Primary Examiner*—Robert T. Bond
*Attorney, Agent, or Firm*—Sprung Horn Kramer & Woods

[57] ABSTRACT

The invention relates, inter alia, to 3,4,5-trihydroxypiperidine compounds of Formula (I), infra, to methods for the manufacture of said compounds, to pharmaceutical compositions containing said compounds and to methods for the use of said compounds and compositions. Also included in the invention are concentrates, premixes and feedstuffs containing said compounds.

17 Claims, No Drawings

3,4,5-TRIHYDROXYPIPERIDINE COMPOUNDS AND THEIR USE AS MEDICAMENTS AND IN ANIMAL NUTRITION

This is a continuation of application Ser. No. 153,286 filed May 27, 1980 now abandoned.

The present invention relates to new 3,4,5-trihydroxypiperidine compounds, to processes for their production and to their use as medicaments, in particular as agents against diabetes, hyperlipaemia and adiposity, and in animal nutrition, for the better utilisation of feed and for influencing the lean meat/fat ratio in favour of the proportion of lean meat.

According to the present invention there are provided compounds which are 3,4,5-trihydroxypiperidine derivatives of the general formula $$\left[\begin{array}{c}\text{CH}_2\text{OH}\\ \text{HO} \diagup \diagdown R_1 \\ \text{HO}-\phantom{xx}\phantom{x}N-R_2 \\ \text{HO}\phantom{xx}R_3\end{array}\right] -X- \left[\begin{array}{c}\text{CH}_2\text{OH}\\ R_1{'} \diagup\diagdown\phantom{x}\text{OH} \\ R_2{'}-N\phantom{xx}\text{OH} \\ R_3{'}\phantom{xx}\text{OH}\end{array}\right] \quad (I)$$

in which $R_1$, $R_1{'}$, $R_3$ and $R_3{'}$, denote a hydrogen atom or a direct bond to X, $R_2$ and $R_2{'}$, denote a hydrogen atom, a $C_1$ to $C_4$ alkyl group or a direct bond to X, with the proviso that one and only one of the radicals $R_1$, $R_2$ and $R_3$ and one and only one of the radicals $R_1{'}$, $R_2{'}$ and $R_3{'}$, represent a direct bond to X, and X is a bridge member.

Preferred bridge members X correspond to the general formula $$-(A)_m-(R_4)_n-(Y)_p-(R_5)_q-(B)_r-$$

in which

A and B independently denote $CH_2$, $CH_2-NH$, $CH_2-NH-CO$, $CH_2-NHCONH$, $CH_2-NHSO_2NH$, $CH_2-NHCONR_6$, $CH_2NHSO_2NR_6$, $CH_2-NH-SO_2$, $CH_2-NHCS-NH$, $CH_2-NH-COO$, $CH_2-NHCS$, $$CH_2-NH-\underset{\underset{NH}{\|}}{C}-NH,$$

$CH_2-O$, CO or COO, $R_4$ and $R_5$ independently correspond to the general formula $$-(R_{13})_s-(U)_t-(R_{14})_v$$

in which $R_{13}$ and $R_{14}$ independently denote optionally substituted straight-chain, branched or cyclic, saturated or unsaturated aliphatic hydrocarbon radicals or optionally substituted aromatic or heterocyclic radicals or optionally substituted mixed aliphatic/aromatic/heterocyclic radicals, and U denotes O, S, SO, $SO_2$, NH, $NR_6$, CO, COO, CS, OCOO, NHCOO, CONH, NHCONH, NHCSNH, CH=N, $SO_2NH$ or $NHSO_2NH$, and s, t and v independently are 0 or 1, Y has the meaning given for U, or has any of the meanings given for $R_{13}$ and $R_{14}$. $R_6$ denotes an alkyl or aryl radical and m, n, p, q and r are 0 or 1 with the proviso that the sum of m and r is 1 or 2 and that p is 0 when n and/or Q are 0.

$R_{13}$ and $R_{14}$ preferably denote alkylidene radicals with 1 to 30, especially 1 to 18, carbon atoms, mono- or polyunsaturated (e.g. di-, tri-unsaturated, etc) alkenylidene radicals or alkinylidene radicals with 2 to 18, especially 3 to 10, carbon atoms, mono-, bi- or tri-cyclic radicals which have 3 to 10 carbon atoms and can be saturated, mono-unsaturated or di-unsaturated, arylidene (preferably carbocyclic arylidene) radicals with 6 or 10 carbon atoms, or heterocyclic radicals which have 3 to 8, especially 3 to 6, ring members and can contain 1, 2, 3 or 4 hetero-atoms, in particular N, O or S, and to which a benzene ring or a further heterocyclic radical of the type mentioned can be fused, it being possible for the said radicals to carry 1 to 5, especially 1, 2 or 3, substituents.

Examples of substituents for alkylidene which may be mentioned are: hydroxyl, or alkoxy with preferably 1 to 4 carbon atoms, especially methoxy and ethoxy; acyloxy, the acyl radical being derived from aliphatic (e.g. alkane) carboxylic acids with 1 to 7 carbon atoms, aromatic carboxylic acids, especially phenylcarboxylic acids, which are optionally substituted in the phenyl radical by —OH, —halogen, especially F, Cl or Br, $C_1$ to $C_4$ alkyl, $C_1$ to $C_4$ alkoxy, nitro and/or amino, or heterocyclic carboxylic acids which are derived from 5-membered or 6-membered heterocyclic compounds which contain 1, 2 or 3 heteroatoms (N, O or S) and are optionally substituted in the heterocyclic ring by $C_1$ to $C_4$ alkyl, chlorine, bromine or amino; amino, monoalkylamino and dialkylamino with preferably 1 to 4 carbon atoms per alkyl radical, especially monomethylamino, monoethylamino, dimethylamino and diethylamino, or monacylamino, the acyl radical being derived from aliphatic (e.g. alkane) carboxylic acids with 1 to 7 carbon atoms, aromatic carboxylic acids, especially phenylcarboxylic acids, which can be substituted in the phenyl radical by —OH, halogen, especially F, Cl or Br, $C_1$ to $C_4$ alkyl, $C_1$ to $C_4$ alkoxy, nitro and/or amino, or heterocyclic carboxylic acids which are derived from 5-membered or 6-membered heterocyclic compounds which contain 1, 2 or 3 hetero-atoms (N, O or S) and are optionally substituted in the heterocyclic ring by $C_1$ to $C_4$ alkyl, chlorine, bromine or amino, mercapto, or alkylthio with preferably 1 to 4 carbon atoms, especially methylthio and ethylthio; halogen, preferably fluorine, chlorine and bromine; alkylcarbonyl with preferably 1 to 4 carbon atoms in the alkyl radical; carboxyl, nitro, cyano, formyl or sulpho; or heterocyclic radicals of the abovementioned type, and especially also heterocyclic radicals which are derived from sugars, especially from hexoses or pentoses, and which can be bonded to the alkylidene radical directly via a ring atom or via an —O—, —S— or —NH— bridge.

Examples of heterocyclic substituents for the alkylidene radicals are: phthalimido, pyridyl, thienyl, furyl, isoxazolyl, thiazolyl, glucopyranosyl, ribofuranosyl and oxiranyl.

Furthermore, aromatic radicals, such as naphthyl and, especially phenyl, which optionally carry one or more, preferably 1,2 or 3 identical or different substituents selected from —OH, —NH$_2$, C$_1$ to C$_4$ alkyl—NH—, C$_1$ to C$_4$ dialkyl—N—, C$_1$ to C$_4$ alkoxy, NO$_2$, —CN, —COOH, —COO—alkyl (C$_1$ to C$_4$), C$_1$ to C$_6$ alkyl, halogen, especially fluorine, chlorine or bromine, C$_1$ to C$_4$ alkylthio, —SH, C$_1$ to C$_4$ alkylsulphonyl, —SO$_3$H, —SO$_2$NH$_2$ and —SO$_2$—NH—alkyl (C$_1$ to C$_4$), are suitable substituents for the alkylidene radicals.

The alkylidene radical can also carry a mono-, bi- or tri-cyclic substituent which has preferably 3 to 10 carbon atoms and can in turn be substituted by hydroxyl, amino, halogen, especially fluorine, chlorine or bromine, or —COOH.

The alkylidene radical preferably carries substituents such as hydroxyl, alkoxy with 1 to 4 carbon atoms, mercapto, alkylthio with 1 to 4 carbon atoms, halogen (especially chlorine, bromine or fluorine), nitro, amino, monoalkylamino with 1 to 4 carbon atoms and acylamino, the acyl radical being derived from aliphatic (especially alkane) carboxylic acids with 1 to 6 carbon atoms.

Possible substituents for the mono-, bi- or tri-cyclic radicals R$_{13}$ and R$_{14}$ are the substituents mentioned for the alkylidene radicals.

The arylidene radicals can carry one or more, preferably 1, 2 or 3, identical or different substituents.

Examples of substituents which may be mentioned are: alkyl which has 1 to 10 (especially 1 to 4) carbon atoms and can in turn be substituted, for example by chlorine, nitro or cyano, optionally substituted alkenyl radicals with 1 to 10 (especially 2 to 4) carbon atoms; amino, or monoalkyl- and dialkyl-amino with preferably 1 to 4 carbon atoms per alkyl radical; mercapto, or alkylthio with preferably 1 to 4 carbon atoms; carboxyl, carbalkoxy with preferably 1 to 4 carbon atoms, sulpho, alkylsulphonyl with preferably 1 to 4 carbon atoms, or arylsulphonyl, preferably phenyl-sulphonyl; aminosulphonyl, or alkylamino- and dialkylamino-sulphonyl with 1 to 4 carbon atoms per alkyl group, preferably methyl- and dimethylaminosulphonyl; nitro, cyano or formyl; alkylcarbonylamino with preferably 1 to 4 carbon atoms; alkylcarbonyl with 1 to 4 carbon atoms, benzoyl, benzylcarbonyl or phenylethylcarbonyl, it being possible for the alkyl, phenyl, benzyl and phenylethyl radicals last mentioned to be in turn substituted, for example by chlorine, nitro or hydroxyl.

The heterocyclic radicals R$_{13}$ and R$_{14}$ are preferably derived from hetero-paraffinic, hetero-aromatic or hetero-olefinic 5-membered or 6-membered rings with preferably 1, 2 or 3 identical or different hetero-atoms. Hetero-atoms are oxygen, sulphur or nitrogen. These ring systems can carry further substituents, for example hydroxyl, amino or C$_1$ to C$_4$ alkyl groups, or benzene nuclei, preferably 6-membered, heterocyclic rings of the type mentioned can be fused onto them.

Particularly preferred heterocyclic radicals are derived, for example, from furane, pyrane, pyrrolidine, piperidine, pyrazole, imidazole, pyrimidine, pyridazine, pyrazine, triazine, pyrrole, pyridine, benzimidazole, quinoline, isoquinoline or purine.

Preferred compounds of the present invention are those compounds of the formula (I) in which both the 2-hydroxymethyl-3,4,5-trihydroxypiperidyl radicals are described by the following sterochemical formula

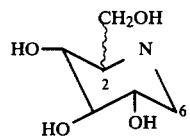

and the bridge member X is probably arranged axially.

The configuration at the 2 and 6 carbon atoms is established on the basis of spectroscopic investigations and has not been proved with absolute certainty.

Particularly preferred compounds of the present invention are those in which

A denotes CH$_2$ if X is linked via R$_2$, or CH$_2$—NHCO, CH$_2$NHSO$_2$, CH$_2$NHCOO, CH$_2$NOSNH or CH$_2$—NHCONH if X is linked via R$_1$ or R$_3$;

B denotes CH$_2$ if X is linked via R$_2$', or CH$_2$NHCO, CH$_2$NHSO$_2$, CH$_2$NHCOO, CH$_2$NHCSNH or CH$_2$NHCONH if X is linked via R$_1$' or R$_3$', R$_{13}$ and R$_{14}$ independently denote a C$_1$ to C$_{18}$ alkylidene, C$_2$ to C$_{18}$ alkenylidene or phenylene radical, U denotes O, S, SO, SO$_2$, NH, CO, CONH, NHCONH, NHCSNH, SO$_2$NH, s, t, v independently denote 0 or 1, Y denotes 0, SO$_2$, CO, CH$_2$, S, SO, NH, CONH, NHCONH, NHCSNH, SO$_2$NH or CH=CH, or a phenylene or optionally substituted phenylene radical, m and na are 1 and r, p and q are independently 0 or 1, and especially preferred are those which correspond to the stereochemical formula (II).

It has been found that the new compounds of the present invention are potent inhibitors for α-glucosidases, in particular for disaccharidases. The new compounds are thus valuable agents for influencing a large number of metabolic processes and hence enrich the range of medicaments.

According to the present invention there is further provided a process for preparing the compounds of the invention in which (a) a compound of the general formula

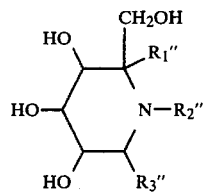

in which

R$_1$'' and R$_3$'' denotes a hydrogen atom or CH$_2$—NH$_2$ and

R$_2$'' denotes a hydrogen atom or a C$_1$ to C$_4$ alkyl group, the number of CH$_2$—NH$_2$ being 0 or 1 and R$_2$'' denoting a hydrogen atom if R$_1$'' and R$_3$'' and R$_3$'' are hydrogen atoms, is reacted with a dialdehyde of the general formula

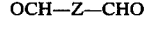

in which

Z denotes the needed members to form the bridge member X, in the ratio 2:1 in the presence of a hydrogen donor, or (b) a compound of the formula (III) is reacted in a molar ratio of 1:2 with an alkylating agent or an acylating agent of the general formula $$R_7-Z-R_7 \quad (V)$$

in which
Z has the abovementioned meaning and
$R_7$ is an alkylating agent or acylating agent functional group, for example a halide radical of a carboxylic acid chloride radical, (c) where $R_1$ and $R_1'$ are to be hydrogen, $R_2$ and $R_2'$ are to be hydrogen or $C_1$ to $C_4$ alkyl, $R_3$ and $R_3'$ are to be direct bonds to X and X is to be alkylene or phenylene radical, a compound of the general formula

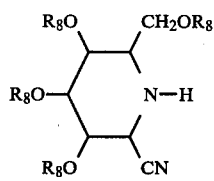
(VI)

in which
$R_8$ is a protective group, for example a trimethylsilyl radical,
is reacted with a compound of the general formula $$BrMg-Z'-MgBr \quad (VII)$$

in which
Z' is an alkylene group or phenylene group,
the cyano group being split off and the protective groups then being removed, preferably by hydrolysis, or, (d) a compound of the formula (III) is reacted with a compound of the general formula $$R_9-Z-R_{10} \quad (VIII)$$

in which
Z has the abovementioned meaning,
$R_9$ denotes —CHO or $R_7$,
$R_{10}$ denotes $R_7$, a group which can be converted into a radical $R_7$ or an aldehyde or keto group, and
$R_7$ has the abovementioned meaning,
in a molar ration 1:1 optionally in the presence of a hydrogen donor, and the radical $R_{10}$ in the intermediate product is reacted under changed reaction conditions for example different temperature, different solvent or in the presence of acids or bases or after conversion into a radical $R_7$, with a further compound of the formula (III), optionally in the presence of a hydrogen donor.

If, by way of illustration, pentane-1,5-dial and 1-desoxynojirimicin are employed in the reaction of process variant (a), the course of the reaction can be represented as follows:

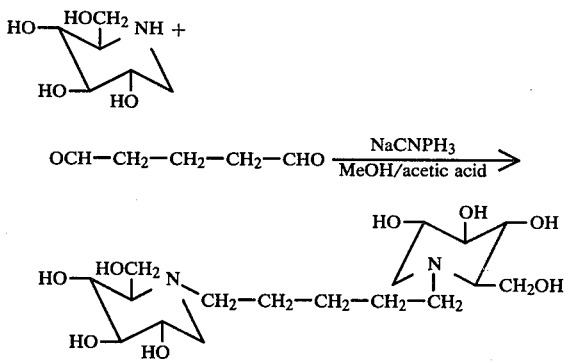

Compounds of the formula (V) for use in process variant (b) belong, for example, to the following classes of substances: alkyl halides, sulphonic acid esters, carboxylic acid halides, sulphonic acid halides, chlorocarbonic acid esters, isocyanates, isothiocyanates and olefines with activated double bonds, the compounds of the formula (V) having two, optionally different, reactive groups.

If sebacic acid chloride is the starting substance, the reaction variant (b) can be illustrated by the following equation:

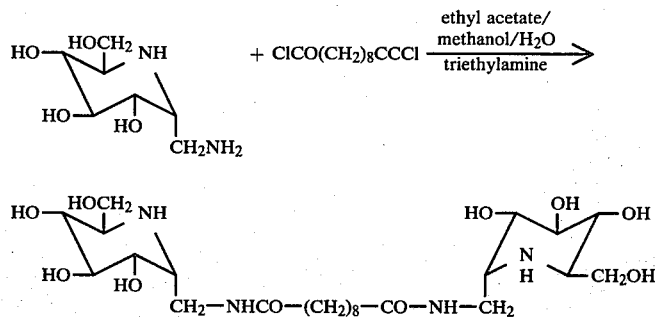

Compounds of the formula (I) are also obtained if the linking of the two trihydroxypiperidine units is carried out in several different steps, the second functional group of the bridge member being formed, from an inactive form, only after linkage to a compound of the formula (III) has been effected, or the second functional group or different reactivity reacting with a second compound of the formula (III) only under changed reaction conditions. Process variant (d) is such a process.

The process variant (d) may be illustrated by the following examples: if 1-desoxynojirimicin is added onto acrylonitrile, the N-alkylated compound is obtained and this can be hydrogenated to give the amino compound or saponified to give the carboxylic acid.

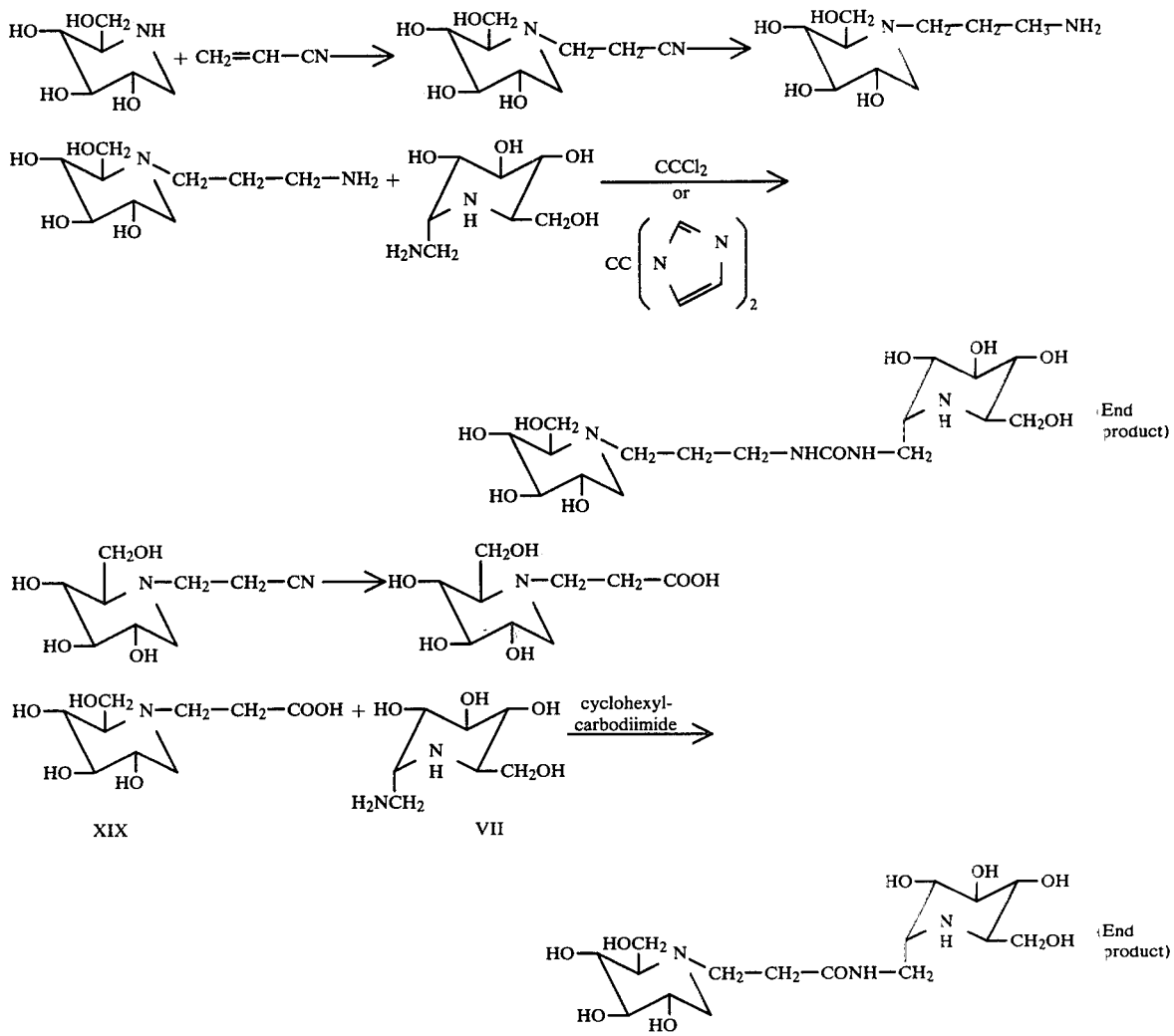

The amino compound can then be reacted with phosgene or carbonyl-bisimidazole and 1-aminomethyl 1-desoxynojirimicin to give a compound of the formula (I); the carboxylic acid can react with cyclohexylcarbodiimide and 1-amino-methyl-1-desoxynojirimicin to give a compound of the formula (I).

The piperidine derivatives used as starting substances in reaction variants (a), (b), and (d), that is to say 1-desoxynojirimicin, 1-aminomethyl-1-desoxynojirimicin and 1-cyano-1-desoxynojirimicin are known from European Published Application 947, published Mar. 7, 1979, now pending.

5-Aminomethyl-1-desoxynojirimicin is obtained by catalytic hydrogenation (Raney nickel, 3.5 bars of $H_2$, solvent: water) of 2,6-imino-2-hydroxymethyl-2,6-didesoxy-L-idohexonic acid nitrile, which is in turn prepared from 6-amino-6-desoxy-L-sorbofuranose hydrochloride monohydrate (known) and sodium cyanide in 0.5 N hydrochloric acid at room temperature.

The carbonyl compounds, alkyl halides and sulphonic acid esters used for the N-alkylation of these piperidine derivatives are also known or can be prepared by known methods.

The reactive acid derivatives used for the reaction with the piperidine derivatives are also known or can be prepared by known methods.

Catalytically activated hydrogen can be used as the hydrogen donor for the reductive alkylation of reaction variant (a). A possible catalyst is, above all, Raney nickel, but noble metal catalysts can also be used. The reaction is normally carried out under pressures between 1 and 150 atmospheres of $H_2$ pressure and at temperatures between 20° and 150° C. Protic, polar solvents, in particular alcohols (e.g. alkanols), are the preferred solvents.

Alkali metal cyanoborohydrides, dialkylaminoboranes and alkali metal borohydrides are also used as the hydrogen donor reducing agents. It is particularly preferable to use sodium cyanoborohydride. The reaction is in general carried out at room temperature. However, it can also be favourable to heat the mixture to the reflux temperature.

The process is usually carried out in an inert solvent. Although anhydrous aprotic solvents can be employed (for example tetrahydrofurane if the reducing agent is morpholinoborane), a protic solvent is nevertheless usually used. A particularly suitable protic solvent is a $C_1$ to $C_6$ alkanol. However, it is also possible to use water or an aqueous $C_1$ to $C_6$ alkanol (for example aqueous methanol or ethanol) or other aqueous solvent systems, such as, for example, aqueous dimethylformamide, aqueous hexamethylphosphoric acid triamide, aqueous tetrahydrofurane or aqueous ethylene glycol dimethyl ether.

The process is usually carried out in a pH range from 1 to 11, and a pH range between 4 and 7 is preferred.

The reaction variant (b) or (d) of the piperidine derivatives with alkyl halides is carried out in polar, protic or aprotic solvents, appropriately in the presence of an acid-binding agent, at temperatures between 0° C. and the boiling point of the solvent.

The reaction is preferably carried out in dimethylformamide/$H_2O$, with $Ag_2O$ as the acid-binding agent, or in dimethylformamide, with $K_2CO_3$ as the acid-binding agent.

The reaction variant (b) or (d) of the piperidine derivatives with the reactive acid derivatives is carried out in polar, protic or aprotic solvents. If appropriate, an acid-binding agent is added. The reaction temperature is between −70° C. and the boiling point. The preferred solvent for the reaction with carboxylic acid chlorides is a mixture of ethyl acetate, methanol and $H_2O$, and an organic base, for example, triethylamine, is preferably used as the acid-binding agent.

A mixture of ethyl acetate, methanol and water is also the preferred solvent for the reaction of the piperidine derivatives with isocyanates, whilst for the reaction with sulphonic acid chlorides, preferably, dimethylformamide is used as the solvent and $K_2CO_3$ is used as the acid-binding agent.

The compounds according to the invention are suitable as therapeutic agents for the following indications: prediabetes, gastritis, constipation, infections of the gastrointestinal tract, meteorism, flatulence, caries, arteriosclerosis, hypertension and, especially adiposity, diabetes and hyperlipaemia.

To broaden the action spectrum, it can be advisable to combine inhibitors for glycoside hydrolases which complement one another in their action, the combinations being either combinations of the compounds according to the invention with one another or combinations of the compounds according to the invention with inhibitors which are already known. Thus, for example, it can be appropriate to combine saccharase inhibitors according to the invention with amylase inhibitors which are already known.

In some cases, combinations of the compounds according to the invention with known oral antidiabetic agents ($\beta$-cytotropic sulphonylurea derivatives and/or biguanides having an action on the blood sugar), and with active compounds which lower the blood lipid level, such as clofibrate, nicotinic acid and cholestyramine are also advantageous.

As stated above, the invention also relates to the use in medicine of the compounds of the invention.

The present invention provides a pharmaceutical composition containing as active ingredient a compound of the invention in admixture with a solid, liquid or liquefied gaseous diluent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in assciation with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The pharmaceutical compositions according to the invention may, for example, take the form of suspensions, solutions and emulsions of the active ingredient in aqueous or non-aqueous diluents, or syrups.

The compounds can be administered without dilution, for example as powders or in a gelatine casing, or in combination with an excipient in a pharmaceutical composition.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e,g, paraffin; (f) resorption accelerators. e.g. quaternary ammonium compounds; (g) surface active agents, e.g. cetyl alcohol, glycerol monostearate; (h) adsorptive carriers, e.g. kaolin, dicalcium phosphate and bentonite; (i) lubricants, e.g. silica gel, talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents, such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils, [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavrouing additions (e.g. peppermint oil and eucalyptus oil) and sweetening agents (e.g. saccharin).

The pharmaceutical compositions according to the invention generally contain from 0.1 to 99.5% of the active ingredient by weight of the total composition.

In addition to a compound of the invention the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The production of the above-mentioned pharmaceutical compositions and medicaments is carried out by any method known in the art.

A powder is prepared by comminuting the substance to a suitable size and mixing it with a pharmaceutical excipient, which is likewise comminuted. Although an edible carbohydrate, such as, for example, starch, lactose, sucrose or glucose is usually used for this purpose and can also be used in this case, it is desirable to use a carbohydrate which cannot be metabolised, such as, for example, a cellulose derivative.

Sweeteners, flavouring additives, preservatives, dispersing agents and colouring agents can also be coused.

The capsules can be produced by preparing the powder mixture described above and by filling gelatine casings which have already been formed. Before the filling operation, lubricants and disintegrating agents, such as those mentioned previously can be added to the mixture in order to improve the accessibility of the inhibitor when the capsule is taken.

Tablets are produced, for example, by preparing a powder mixture, of coarse or fine grain size, and adding a lubricant and disintegrator. Tablets are formed from this mixture. A powder mixture is prepared by mixing the substance, which has been comminuted in a suitable manner, and making up with a diluent or another excipient such as those mentioned previously. The powder mixture can be granulates, together with a binder, such as, for exammple syrup, starch paste or acacia mucilage, or solutions of cellulose materials or polymeric materials. The product is then pressed through a coarse sieve. As an alternative to this, the powder mixture can be allowed to run through a tabletting machine and the resulting pieces of non-uniform shape can be comminuted down to a particle size. A lubricant, such as, for example, stearic acid, a stearate salt, talc or mineral oil, can be added to the resulting particles so that these do not stick in the tablet-forming nozzles. This mixture, which has been given slip properties, is then pressed into tablet form. The active compounds can also be combined with free-flowing inert excipients and brought direct into tablet form omitting the granulating or fragmentation steps. The producct can be provided with a clear or opaque protective shell, for example a coating of shellac, a coating of sugar or polymeric substances and a polished shell of wax. Dyestuffs can be added to these coatings so that the different dosage units can be differentiated.

A syrup can be prepared by dissolving the active compound in an aqueous solution which contains suitable flavouring agents; elixirs are obtained using non-toxic, alcoholic excipients. Suspensions can be prepared by dispersing the compound in a non-toxic excipient optionally together with solubilising agents, emulsifying agents, such as, for example, ethoxylated isostearyl alcohols and polyoxyethylenesorbitol esters, preservatives, sweetening agents and flavouring additions such as those mentioned previously.

Dosage instructions can be indicated on the capsule. In addition, it is possible to safeguard the dosage by releasing the active compound in a delayed manner as mentioned previously.

This invention further provides a method of combating the above-mentioned diseases in warm-blooded animals, which comprises administering to the animals a compound of the invention alone or in admixture with a diluent or in the form of a medicament according to the invention.

In general it has proved advantageous to administer amounts of from 1 to $1 \times 10^4$ saccharase inhibitor units kg of body weight per day to achieve effective results. Nevertheless, it can at times be necessary to deviate from those dosage rates, and in particular to do so as a function of the nature and body weight of the subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

In addition to the abovementioned pharmaceutical compositions, foodstuffs containing these active compounds can also be prepared; for example sugar, bread, potato products, fruit juice, beer, chocolate and other confectionery, and preserves, for example, jam, and in this case a therapeutically effective amount of at least one of the inhibitors according to the invention is added to these products.

The foodstuffs produced using the active compounds according to the invention are suitable both for the diet of patients suffering from metabolism disorders and for the nutrition of healthy persons in the sense of a diet which prevents metabolism disorders.

The inhibitors according to the invention furthermore have the property of influencing to a great extent the relationship between the proportion of undesired fat to the proportion of desired meat of low fat content (lean meat) in animals in favour of the lean meat. This is of particular importance for rearing and keeping agricultural livestock, for example in the fattening of pigs, but is also of considerable importance for rearing and keeping other livestock and pets. Using the inhibitors can furthermore lead to a considerable rationalisation of feeding of animals, from the point of view of time, quantity and quality. Since the inhibitors cause a certain delay in digestion, the residence time of the nutrients in the digestive tract is extended and this makes possible ad libitum feeding, which is associated with a low expenditure. Moreover, using the inhibitors according to the invention in many cases results in a considerable saving of valuable protein feed.

Accordingly the present invention provides a medicated feed comprising a compound according to the present invention and a nutritious material.

The active compounds can thus be used in virtually all fields of animal nutrition as agents for reducing the deposition of fat and for saving feed protein.

The activity of the active compounds is largely independent of the species and sex of the animals. The active compounds prove particularly valuable in the case of species of animals which, generally or at certain periods of their life, tend to deposit relatively large amounts of fat.

The following livestock and pets may be mentioned as examples of animals for which the inhibitors can be employed for reducing the deposition of fat and/or for saving feed protein: warm-blooded animals, such as cattle, pigs, horses, sheep, goats, cats, dogs, rabbits, fur-bearing animals, for example mink and chinchillas, other pets, for example guineapigs and hamsters, laboratory animals and zoo animals, for example rats, mice, apes and the like, and poultry, for example broilers, hens, geese, ducks, turkeys, pigeons, parrots and canaries, and cold-blooded animals, such as fish, for example carp, and reptiles, for example snakes.

Because of the favourable properties of the active compounds, the amount of the active compounds which is administered to the animals to achieve the desired effect can be varied substantially. It is about 0.1 mg to 1.0 g and preferably 1 to 100 mg/kg of feed per day. The period of administration can be from a few hours or days up to several years. The appropriate amount of active compound and the appropriate period of administration are closely related to the aim of feeding. They depend, in particular, on the species, age, sex, state of health and nature of keeping of the animals and can easily be determined by any expert.

The active compounds according to the invention are administered to the animals by the customary methods. The nature of the administration depends, in particular, on the species, the behaviour and the general condition of the animals. Thus, administration can be effected orally once or several times daily at regular or irregular intervals. For reasons of expediency, in most cases oral administration, in particular in the rhythm of the intake of food and/or drink by the animals, is to be preferred.

The active compounds can be administered as pure substances or in the formulated form, the formulated form being understood as a primix that is to say as a mixture with non-toxic inert carriers of any desired nature, as a part of a total ration in the form of a supplementary feed or as a mixing component of a mixed feed for use by itself. Administration of suitable formulations via the drinking water is also included.

The active compounds, optionally in the formulated form, can also be administered in a suitable form together with other nutrients and active compounds, for example mineral salts, trace elements, vitamins, proteins, energy carriers (for example starch, sugars, fats), dyestuffs and/or flavouring agents or other feed additives, such as, for example, growth promoters. The active compounds can be administered to the animals before, during or after intake of the feed.

Oral administration together with the feed and/or drinking water is recommended, the active compounds being added to all or only parts of the feed and/or drinking water as required.

The active compounds can be admixed to the feed and/or drinking water in accordance with customary methods by simple mixing as pure substances, preferably in the finely divided form or in the formulated form mixed with edible, non-toxic carriers, and optionally also in the form of a premix or a feed concentrate.

The feed and/or drinking water can contain the active compounds according to the invention in a concentration of, for example, about 0.001 to 5.0%, in particular 0.02 to 2.0% (by weight). The optimum level of the concentration of the active compound in the feed and/or drinking water depends, in particular, on the amount of feed and/or drinking water taken in by the animals and can easily be determined by any expert.

The nature of the feed and its composition is irrelevant in this context. All the customary, commercially available or specified feed compositions, which preferably contain the customary equilibrium of energy substances and proteins, including vitamins and mineral substances, necessary for balanced nutrition, can be used. The feed can be composed, for example, of vegetable substances, for example shredded oilcake, shredded cereal and cereal by-products, and also hay, silage fodder, beet and other forage plants, of animal substances, for example meat products and fish products, bone meal, fats, vitamins, for example A, D, E, K and B complex, and specific sources of protein, for example yeasts, and certain aminoacids and mineral substances and trace elements, such as, for example, phosphorus and iron, zinc, manganese, copper, cobalt, iodine and the like.

Premixes can preferably contain about 0.1 to 50%, in particular 0.5 to 5.0% (by weight) of an active compound according to the invention, in addition to any desired edible carriers and/or mineral salts, for example carbonated feed lime, and are prepared by the customary mixing methods.

Mixed feeds preferably contain 0.001 to 5.0%, in particular 0.02 to 2.0% (by weight) of an active compound according to the invention, in addition to the customary raw material components of a mixed feed, for example shredded cereal or cereal by-products, shredded oilcake, animal protein, minerals, trace elements and vitamins. They can be prepared by the customary mixing methods.

In premixes and mixed feedstuffs, preferably, the active compounds can also optionally be protected from air, light and/or moisture by suitable agents which coat their surface, for example with non-toxic waxes or gelatine.

The following is an example of the composition of a finished mixed feed for poultry, which contains an active compound of the present invention: 200 g of wheat, 340 g of maize, 360.3 g of coarse soya bean meal, 60 g of beef tallow, 15 g of dicalcium phosphate, 10 g of calcium carbonate, 4 g of iodinated sodium chloride, 7.5 g of a vitamin/mineral mixture and 3.2 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 g of $MnSO_4 \times H_2O$, 140 mg of $ZnSO_4 \times 7H_2O$, 100 mg of $FeSO_4 \times 7H_2O$ and 20 mg of $CuSO_4 \times 5H_2O$.

The active compound premix contains an active compound according to the invention in the desired amount, for example 1,600 mg, and in addition 1 g of DL-methionine as well as an amount of soya bean meal such that 3.2 g of premix are formed.

The following is an example of the composition of a mixed feed for pigs, which contain an active compound of the present invention: 630 g of shredded cereal feed (composed of 200 g of shredded maize, 150 g of shredded barley, 150 g of shredded oats and 130 g of shredded wheat), 80 g of fish meal, 60 g of coarse soya bean meal, 58.8 g of tapioca meal, 38 g of brewer's yeast, 50 g of a vitamin/mineral mixture for pigs (composition, for example, as for the chick feed), 30 g of linseed cake meal, 30 g of maize gluten feed, 10 g of soya bean oil, 10 g of sugarcane molasses and 2 g of an active compound premix (composition, for example, as for the chick feed) give, after careful mixing, 1 kg of feed.

The feed mixtures indicated are intended preferably for rearing and fattening chicks or pigs respectively, but they can also be used, in the same or a similar composition, for rearing and fattening other animals.

The compounds of the present invention can be used individually or in any desired mixtures with one another.

IN VITRO SACCHARASE INHIBITION TEST

The in vitro saccharase inhibition test makes it possible to determine the inhibitory activity of a substance on enzymes by comparing the activity of solubilised intestinal disaccharidase complex in the presence and in the absence (so-called 100% value) of the inhibitor. A virtually glucose-free sucrose (glucose > 100 ppm) is used as the substrate which determines the specificity of the inhibition test; the determination of the enzyme activity is based on the spectrophotometric determination of glucose liberated by means of glucose dehydrogenase and nicotinamide-adenine dinucleotide as the cofactor.

A saccharase inhibitor unit (SIU) is defined as the inhibitory activity which reduces a given saccharolytic activity in a defined test batch by one unit (saccharase unit=SU); the saccharase unit is thereby defined as the enzyme activity which, under the given conditions, splits one μmol of sucrose per minute and thus leads to the liberation of one μmol each of glucose, which is determined in the test, and fructose, which is not recorded in the test.

The intestinal disaccharidase complex is obtained from swine small intestine mucosa by tryptic digestion, precipitation from 66% strength ethanol at −20° C., taking up of the precipitate in 100 mM phosphate buffer of pH 7.0 and finally dialysis against the same buffer.

100 μl of a dilution of the intestinal disaccharidase complex in 0.1M maleate buffer of pH 6.25 are added to 10 μl of a sample solution which is made up such that the extinction of the test batch is at least 10%, but not more than 25%, below that of the 100% value, and the mixture is pre-incubated at 37° C. for 10 minutes. The dilution of the disaccharidase complex is to be adjusted to an activity of 0.1 SU/ml.

The saccharolytic reaction is then started by adding 100 μl of a 0.4M solution of sucrose ("SERVA 35579") in 0.1M maleate buffer of pH 6.25 and, after an incubation period of 20 minutes at 37° C., is stopped by adding 1 ml of glucose dehydrogenase reagent (1 small bottle of a lyophilised glucose dehydrogenase/mutarotase mixture ("MERCK 14053") and 331.7 mg of β-nicotinamide-adenine dinucleotide (free acid, "BOEHRINGER", degree of purity I) dissolved in 250 ml of 0.5M tris buffer of pH 7.6). To determine the glucose, the mixture is incubated at 37° C. for 30 minutes and finally measured photometrically at 340 nm against a reagent blank (with the enzyme but without sucrose).

Calculation of the inhibitory activity of inhibitors is made difficult by the fact that even slight changes in the test system, for example a 100% value which varies slightly from determination to determination, have an influence on the test result which can no longer be ignored. These difficulties are by-passed by running a standard with each determination; a saccharose inhibitor of the forula $C_{25}H_{43}O_{18}N$ which has a specific inhibitory activity of 77,700 SIU/g, and, when employed in the test in amounts of 10 to 20 ng, leads to an inhibition of the order of size specified above, is used as the standard. When the difference in the extinctions at 340 nm between the 100% value and the batch inhibited by the standard is known, it is possible to calculate the specific inhibitory activity of the inhibitor, expressed in saccharase inhibitor units per gram (SIU/g), in a known manner from the difference in extinction between the 100% value and the batch inhibited by the sample solution, taking into consideration the amount of inhibitor employed.

The following Examples 1 to 48 illustrate the production of compounds of the present invention.

EXAMPLE 1

1,5-[N,N'-Bis-(1,5-didesoxy-1,5-imino-D-glucit)-yl]pentane

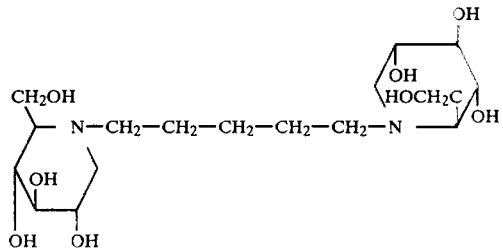

28.4 ml of 25% strength pentanedial are added to a solution of 21 g of 1-desoxynojirimicin in 630 ml of methanol and 42.5 ml of glacial acetic acid and the mixture is cooled to about −5° C. 17.5 g of sodium cyanoborohydride are then added. After stirring the mixture at 0° C. for four hours, it is stirred at room temperature for 18 hours. The reaction mixture is concentrated and the residue is dissolved in about 200 ml of methanol/water in the volume ratio 8:1 and the solution is discharged onto a column 40 cm long and 60 cm wide containing Amberlite IR 120 (H+ form) as the packing material. The column is washed with about 4 liters of methanol/water 8:1 and then eluted with 5% strength ammonia in methanol/water 8:1. A mixture of three substances, one of which is 1-desoxynojirimicin, is obtained. The collected fractions are concentrated.

20.6 g of a slightly coloured oil are obtained. This mixture is discharged, as a concentrated aqueous solution, onto a column 120 cm long and 6 cm wide containing cellulose as the stationary phase and acetone as the mobile phase. The column is eluted with acetone and then with aqueous acetone, the proportion of water being increased continuously. The individual fractions are examined by thin layer chromatography. After the by-products have been separated off, the product is obtained with acetone/water in the volume ratio 3:1. The pure fractions are collected and concentrated. The evaporation residue is dissolved in absolute methanol and, after adding Tonsil and animal charcoal, the mixture is filtered and the filtrate is concentrated. The evaporation residue is taken up in a little absolute methanol and left to crystallise. After leaving to stand for 18 hours, the crystals are filtered off and washed with methanol. 10.1 g of colourless crystals of melting point 186°-187° C. are obtained.

EXAMPLE 2

N,N'-Bis-[(1,5-didesoxy-1,5-imino-D-glucityl)-methyl]-3,3'-sulphonyl-bisbenzenesulphonic acid amide

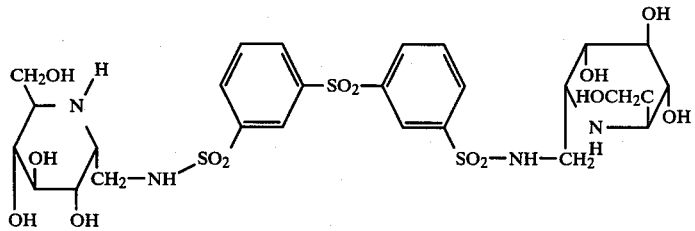

A suspension of 1.92 g of 1-aminoethyl-1-desoxynojirimicin and 2.76 g of potassium carbonate in 20 ml of absolute dimethylformamide is cooled to −10° C. and 1.85 g of 3,3-sulphonyl-bisbenzenesulphonyl chloride are added. The mixture is stirred overnight, the salt which has separated out is filtered off and the filtrate is concentrated. The evaporation residue is dissolved in a little water and the solution is discharged onto a column 120 cm long and 40 cm wide containing cellulose as the stationary phase and acetone as the mobile phase. The column is eluted with aqueous acetone with an increasing content of water. The individual fractions are examined by thin layer chromatography. The fractions containing the desired product are combined and concentrated.

0.9 g of a colourless foam with a Rf value of 0.57 (thin layer chromatography pre-coated plates, Merck, coated with silica gel 60 F 254, running agent: methanol/chloroform/25% strength ammonia 90:60:60) is obtained. Rf value of 1-aminoethyl-1-desoxynojirimicin=0.26.

EXAMPLE 3

$N^1,N^4$-Bis[5-(1,5-didesoxy-1,5-imino-D-glucityl)-methyl]hexamethylene-bisurea

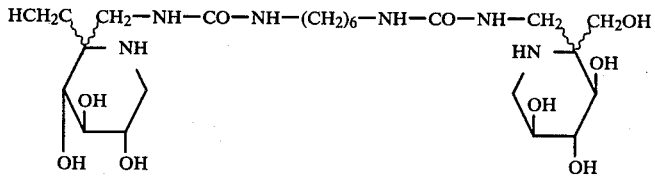

5.3 g of 2-aminomethyl-2-hydroxymethyl-3,4,5,-trihydroxypiperidine dihydrochloride are dissolved in 40 ml of 1N sodium hydroxide solution and the solution is diluted with 80 ml of methanol. The solution is cooled to 0° C. and a solution of 1.59 ml of hexamethylene diisocyanate in 20 ml of ethyl acetate is added dropwise. The mixture is stirred for 18 hours and concentrated, the residue is taken up in absolute methanol and the inorganic salt is filtered off. The filtrate is concentrated and the residue is discharged onto a column 120 cm long and 4 cm wide containing cellulose as the stationary phase and acetone as the mobile phase. The column is eluted with aqueous acetone, the concentration of water being increased stepwise. The individual fractions are examined by thin layer chromatography to determine their content of the desired compound.

The fractions containing the desired product are combined and concentrated. 450 mg of product are obtained in the form of a colourless foam with a Rf value of 0.33. Running agent: methanol/chloroform/25% strength ammonia 3:2:2.

Rf value of 2-aminoethyl-2-hydroxymethyl-3,4,5-trihydroxy-piperidine=0.315.

EXAMPLE 4

N,N'-Bis-[5-(1,5-didesoxy-1,5-imino-D-glucityl)-methyl]sebacic acid diamide

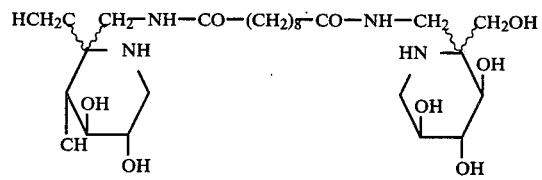

5.3 g of 2-aminomethyl-2-hydroxymethyl-3,4,5-trihydroxypiperidine dihydrochloride are dissolved in 20 ml of water and 60 ml of methanol, and 8.4 ml of triethylamine are added. A solution of 2.13 ml of sebacic acid dichloride in 30 ml of ethyl acetate is then added dropwise, whilst cooling with ice. The reaction mixture is stirred at room temperature for 3 hours and concentrated and the residue is filtered, as an aqueous solution, through a column 25 cm long and 3 cm wide containing Amberlite IR 400 (OH⁻ form) as the packing material. The column is washed thoroughly with water and the filtrate is concentrated. The evaporation residue is discharged onto a column 120 cm long and 4 cm wide containing cellulose as the stationary phase and acetone as the mobile phase. The column is eluted first with acetone and then with acetone to which water is added stepwise in larger portions. The individual fractions are examined by thin layer chromatography. The fractions containing the desired product are combined and concentrated. 0.9 g of the compound is obtained as a solid foam with a Rf value of 0.48 (running agent: methanol/chloroform/25% strength ammonia 3:2:2).

EXAMPLE 5

N,N'-Bis-[1-α-(1,5-didesoxy-1,5-imino-D-glucityl)-methyl]sebacic acid diamide

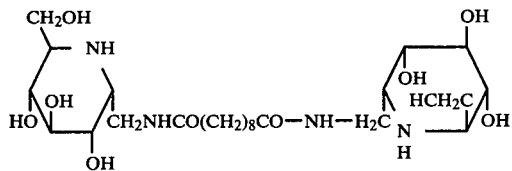

0.28 ml of sebacic acid dichloride in 4 ml of ethyl acetate are added dropwise to 0.5 g of 1-aminomethyl-1-desoxynojirimicin in 6 ml of methanol, 2 ml of water and 0.36 ml of triethylamine at 0° C. The mixture is subsequently stirred at room temperature for 2 hours and the precipitate is filtered off. It is rinsed with ethyl acetate and dried.

For purification, the solid is dissolved in dimethylformamide/H₂O and precipitated with acetone. Yield: 0.5 g. Melting point: 247°–250° C. Rf value on thin layer chromatography pre-coated plates (Merck, coated with silica gel 60 F254) with methanol/chloroform/aqueous ammonia 3:2:2 as the running agent: 0.53
Rf value for 1-aminomethyl-1-desoxynojirimicin: 0.28.

EXAMPLE 6

1,4-[N,N'-Bis-(1',5-didesoxy-1',5'-imino-D-glucit)-yl]but-2-ene

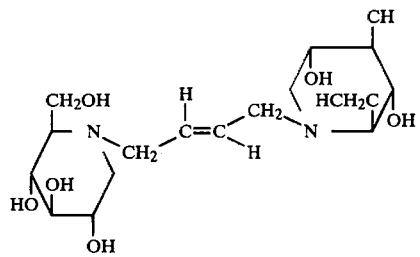

2 g of Ag₂O are added to 2 g of 1-desoxynojirimicin in 12 ml of H₂O and 12 ml of dimethylformamide, and 1.3 g of trans-1,4-dibromobut-2-ene in 5 ml of dimethylformamide are added dropwise at 0° C.

The mixture is allowed to come slowly to room temperature and is stirred at room temperature for 3 hours. It is then diluted with 30 ml of water, the salts are filtered off and the aqueous filtrate is concentrated. The residue is discharged onto a column packed with cellulose.

The column is eluted first with acetone/waer 9:1, then with acetone/water 8:2 and finally with acetone/water 7:3.

The fractions are examined by thin layer chromatography on silica gel plates (running agent: methanol/chloroform/aqueous ammonia 3:2:2).

The fractions which contain the required compound are combined and concentrated.

Yield: 0.9 g

Rf value on thin layer chromatography pre-coated plates (Merck, Darmstadt, silica gel 60 F 254) using methanol/chloroform/aqueous ammonia 3:2:2 as the runing agent: 0.35.

Rf value for 1-desoxynojirimicin: 0.51.

EXAMPLE 7

The following compound was obtained analogously to Example 3:

N¹,N⁴-Bis[1-α-(1,5-didesoxy-1,5-imino-D-glucityl)-methyl]hexamethylene-bisurea

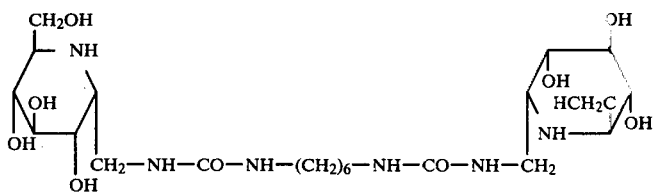

Rf value: 0.39; 1-aminomethyl-1-desoxynojirimicin: 0.28.

EXAMPLE 8

β-β'-[N,N'-Bis-(1,5-didesoxy-1,5-imino-D-glucit)-yl]diethyl sulphone

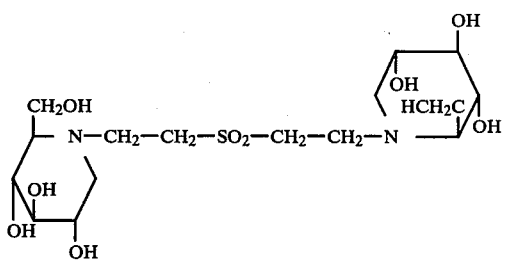

6.52 g (40 mmols) of 1-desoxynojirimicin are dissolved in a mixture of 60 ml of ethanol and 30 ml of water and, after adding one drop of concentrated sodium hydroxide solution, the mixture is cooled to 0°–5° C. 2.3 ml (~22 mmols) of divinyl sulphone are added and the mixture is then stirred at room temperature for 48 hours. The reaction mixture is concentrated, the residue is dissolved in a little water and the solution is discharged onto a column 120 cm long and 6 cm wide containing cellulose as the stationary phase and acetone as the mobile phase. The column is eluted with acetone, to which water is added stepwise in an ever increasing proportion. The individual fractions are examined by thin layer chromatography. After separating off the by-products, the desired compound is obtained by elution with acetone/water in the volume ratio 7:3. The fractions containing the pure product are collected and concentrated. 4.6 g of a colourless foam with a Rf value of 0.33 (running agent: methanol/chloroform/25% strength ammonia 3:2:2) are obtained; Rf value for 1-desoxynojirimicin=0.52.

EXAMPLE 9

$N^1,N^4$-Bis-[5-(1,5-imino-1,5-didesoxy-D-glucityl)-methyl]hexamethylene-bisthiourea

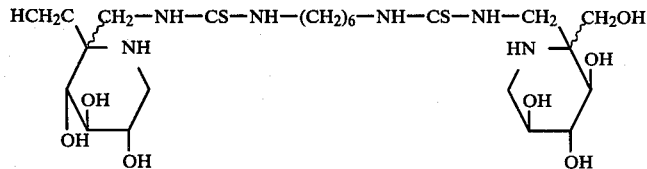

5.3 g of 2-aminomethyl-2-hydroxymethyl-3,4,5-trihydroxy-piperidine dihydrochloride are dissolved in a mixture of 180 ml of methanol and 60 ml of water and, after adding 5.6 ml of triethylamine, a solution of 2.0 g of hexamethylene diisothiocyanate in 60 ml of ethyl acetate is added dropwise at 0° to −5° C. The mixture is stirred at room temperature for 24 hours and concentrated and the residue is dissolved in a little methanol/water in the volume ratio 8:1. The solution is filtered through a short column containing Amberlite IR 400, OH form, and the column is washed thoroughly with methanol/water 8:1. The filtrate is concentrated, the residue is dissolved in a little methanol/water and the solution is discharged onto a column 100 cm long and 4 cm wide containing cellulose as the stationary phase and acetone as the mobile phase. The column is eluted first with acetone/water 9:1, then with acetone/water 8.5:1.5 and finally with acetone/water 8:2. The fractions are examined by thin layer chromatography on silica gel plates (running agent: methanol/chloroform/25% strength ammonia 3:2:2). The fractions containing the pure product are combined and concentrated. 1.4 g of the compound 9 with a Rf value of 0.56 are obtained. Rf of 2-aminomethyl-2-hydroxymethyl-3,4,5-trihydroxypiperidine dihydrochloride=0.34.

Running agent: methanol/chloroform/25% strength ammonia in the volume ratio 3:2:2.

EXAMPLE 10

1,6-[N,N'-Bis-(1',5'-didesoxy-1',5'-imino-D-glucit)-yl]n-hexane

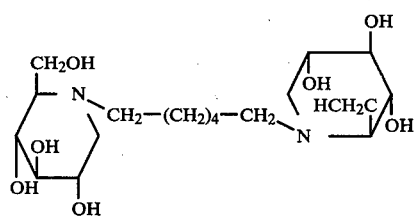

2.5 g of $K_2CO_3$ and 4 g of 1,6-dibromohexane are added to 5 g of 1-desoxynojirimicin in 50 ml of dimethylformamide at 20° C.

The mixture is warmed to 100° C. and stirred for 15 hours. The dimethylformamide is then stripped off in vacuo. The residue is discharged onto a column packed with cellulose. The column is eluted first with acetone/water 9:1, then with acetone/water 8:2 and finally with acetone/water 7:3.

The fractions are examined by thin layer chromatography on silica gel plates (running agent: methanol/chloroform/aqueous ammonia 3:2:2).

The fractions which contain the required compound are combined and concentrated.

Yield: 2.5 g

Rf value on thin layer chromatography pre-coated plates (Merck, Darmstadt, silica gel 60 F 254) with methanol/chloroform/aqueous ammonia 3:2:2 as the running agent: 0.525.

Rf value for 1-desoxynojirimicin: 0.53.

EXAMPLE 11

The following compound was obtained analogously to Example 10:

1,8-[N,N'-Bis-(1',5'-didesoxy-1',5'-imino-D-glucit)-yl]-n-octane

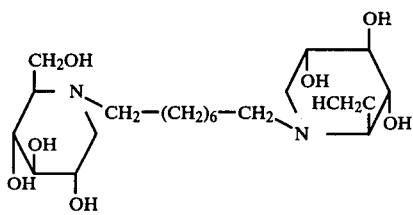

Rf value: 0.63
Rf value for 1-desoxynojirimicin: 0.53

EXAMPLE 12

3-(N-1',5'-Didesoxy-1',5'-imino-D-glucit-yl)-propionic acid
[1-α-(1'',5''-didesoxy-1'',5''-imino-D-glucit)-yl]methylamide

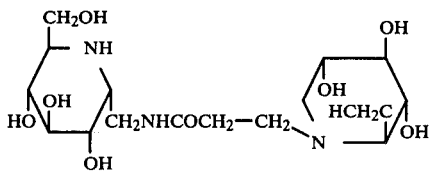

0.52 g of dicyclohexylcarbodiimide is added to 0.59 g of 1-desoxynojirimicinyl-β-propionic acid in 10 ml of pyridine and 7 ml of H$_2$O at 20° C. 0.48 g of 1-aminomethyl-1-desoxynojirimicin in 3 ml of H$_2$O are introduced into the mixture and the mixture is stirred at room temperature for 12 hours. It is then warmed to 50° C. and stirred for a further 20 hours. The mixture is concentrated and the residue is taken up in 25 ml of H$_2$O. The insoluble material is filtered off and the solution is discharged onto a column 25 cm long and 3 cm wide containing Amberlite JRA 400 (OH⁻ form) as the packing material. The column is eluted with about 250 ml of H$_2$O and the aqueous eluate is concentrated.

The residue is discharged onto a column containing cellulose as the stationary phase and acetone as the mobile phase. The column is eluted with acetone/H$_2$O 9:1, then with acetone/H$_2$O 8:2 and finally with acetone/H$_2$O 7:3. The individual fractions are examined by thin layer chromatography. The fractions containing the desired product are combined and concentrated.

EXAMPLE 13

3-(N-1'',5''-Didesoxy-1'',5''-imino-D-glucit-yl)-propionic acid
3'-(N'-1''',5'''-didesoxy-1''',5'''-imino-D-glucit-yl) n-propylamide

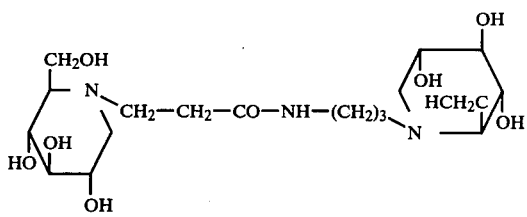

0.1 g of 4-dimethylaminopuridine and 3.3 g of γ-amino-N-n-propyl-1-desoxynojirimicin, dissolved in 10 ml of H$_2$O and 10 ml of pyridine, are added to 3 g of 1-desoxynojirimicin β propionic acid in 20 ml of H$_2$O and 20 ml of pyridine at 20° C., whilst stirring. 2.9 g of dicyclohexylcabodiimide are introduced into the mixture and the mixture is stirred at 20° C. for 15 hours.

The solution is concentrated and the residue is discharged onto a column packed with silica gel.

The column is eluted with ethyl acetate/methanol/water/aqueous ammonia 100:60:5:1.

The fractions are examined by thin layer chromatography on silica gel plates (running agent: ethyl acetate/methanol/water/aqueous ammonia 100:60:25:1).

The fractions which contain the required compound are combined and concentrated.
Yield: 1.4 g
Optical rotation: $[\alpha]_{589} = -0.086$
Rf value of the product/Rf value of 1-desoxynojirimicinyl-β-propionic acid = 1:0.26 (thin layer chromatography precoated plates, Merck, silica gel 60 F 254, running agent: ethyl acetate/methanol/water/25% strength ammonia 100/60/25/1)

The following compound are prepared analogously to Preparation Example 4:

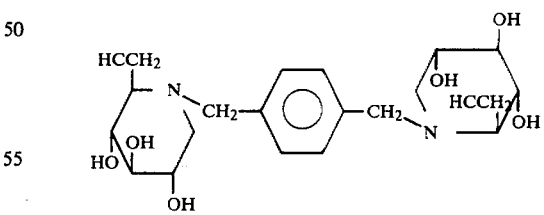

| Example No. | n | Rf value in methanol/chloroform/ 25% strength ammonia 3:2:2 (Rf=).34 for 2-aminomethyl-2-hydroxymethyl-3,4,5-trihydroxy-piperidine × 2HCl) |
|---|---|---|
| 14 | 2 | 0.2 |
| 15 | 3 | 0.23 |
| 16 | 4 | 0.3 |
| 17 | 6 | 0.41 |
| 18 | 7 | 0.47 |

EXAMPLE 19

α,α'-[N,N'-Bis-(1,5-didesoxy-1,5-imino-D-glucit)-yl]-p-xylene

The compound is obtained analogously to Example 6 from α,α'-dibromoxylene and 1-desoxynojirimicin.
Rf value: 0.53
Rf value for 1-desoxynojirimicin: 0.51 (thin layer chromatography pre-coated plates from Messrs. Merck, Darmstadt, silica gel 60 F 254; running agent: methanol/chloroform/25% strength ammonia 3:2:2)
Melting point: 280°-281° C.

Active compounds according to the invention, obtainable using the appropriate reactants and the procedures specified in the above examples, which can be mentioned specifically are:

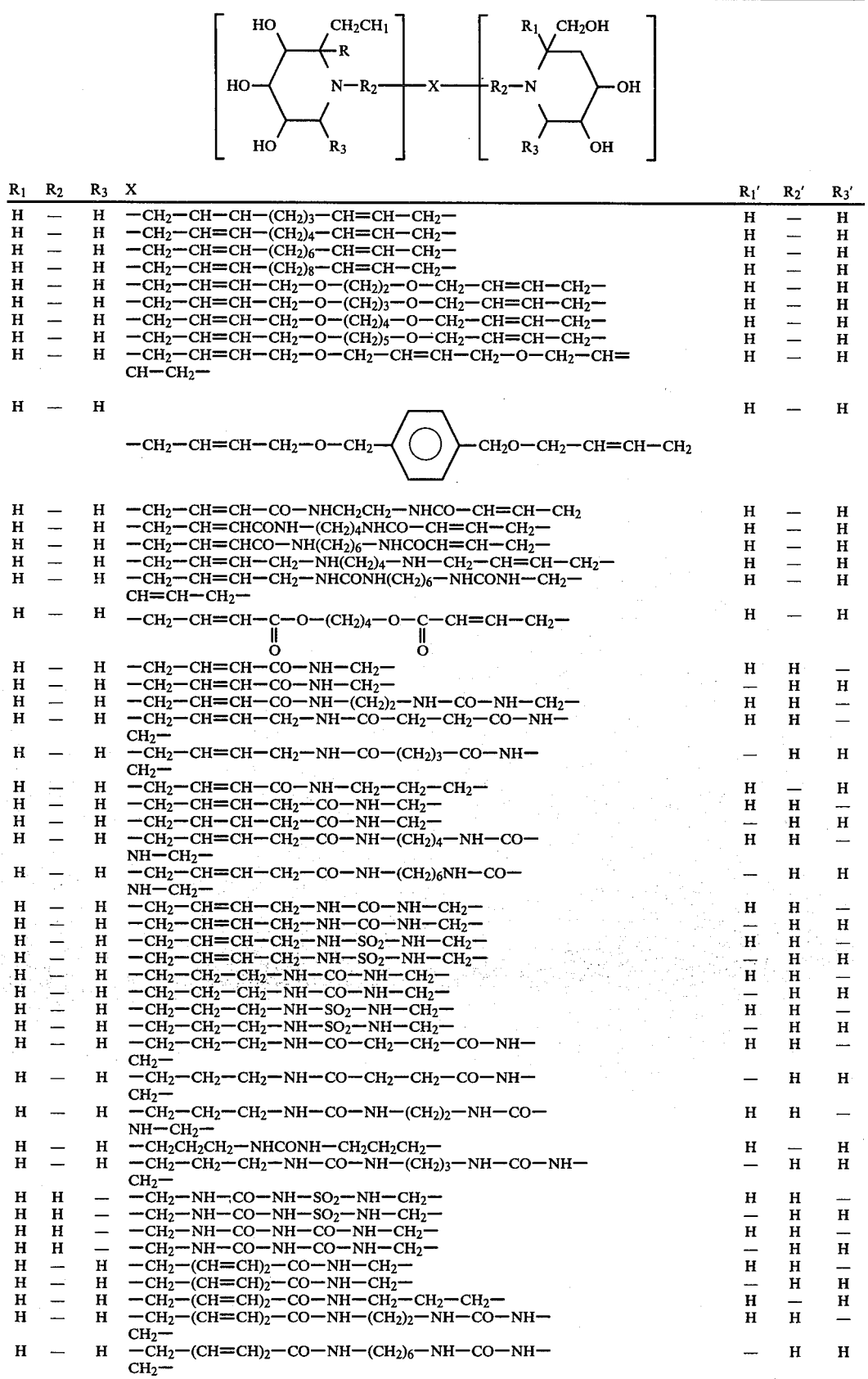

| $R_1$ | $R_2$ | $R_3$ | X | $R_1'$ | $R_2'$ | $R_3'$ |
|---|---|---|---|---|---|---|
| H | — | H | $-CH_2-CH=CH-(CH_2)_3-CH=CH-CH_2-$ | H | — | H |
| H | — | H | $-CH_2-CH=CH-(CH_2)_4-CH=CH-CH_2-$ | H | — | H |
| H | — | H | $-CH_2-CH=CH-(CH_2)_6-CH=CH-CH_2-$ | H | — | H |
| H | — | H | $-CH_2-CH=CH-(CH_2)_8-CH=CH-CH_2-$ | H | — | H |
| H | — | H | $-CH_2-CH=CH-CH_2-O-(CH_2)_2-O-CH_2-CH=CH-CH_2-$ | H | — | H |
| H | — | H | $-CH_2-CH=CH-CH_2-O-(CH_2)_3-O-CH_2-CH=CH-CH_2-$ | H | — | H |
| H | — | H | $-CH_2-CH=CH-CH_2-O-(CH_2)_4-O-CH_2-CH=CH-CH_2-$ | H | — | H |
| H | — | H | $-CH_2-CH=CH-CH_2-O-(CH_2)_5-O-CH_2-CH=CH-CH_2-$ | H | — | H |
| H | — | H | $-CH_2-CH=CH-CH_2-O-CH_2-CH=CH-CH_2-O-CH_2-CH=CH-CH_2-$ | H | — | H |
| H | — | H | $-CH_2-CH=CH-CH_2-O-CH_2-C_6H_4-CH_2O-CH_2-CH=CH-CH_2$ | H | — | H |
| H | — | H | $-CH_2-CH=CH-CO-NHCH_2CH_2-NHCO-CH=CH-CH_2$ | H | — | H |
| H | — | H | $-CH_2-CH=CHCONH-(CH_2)_4NHCO-CH=CH-CH_2-$ | H | — | H |
| H | — | H | $-CH_2-CH=CHCO-NH(CH_2)_6-NHCOCH=CH-CH_2-$ | H | — | H |
| H | — | H | $-CH_2-CH=CH-CH_2-NH(CH_2)_4-NH-CH_2-CH=CH-CH_2-$ | H | — | H |
| H | — | H | $-CH_2-CH=CH-CH_2-NHCONH(CH_2)_6-NHCONH-CH_2-CH=CH-CH_2-$ | H | — | H |
| H | — | H | $-CH_2-CH=CH-\underset{O}{\underset{\|}{C}}-O-(CH_2)_4-O-\underset{O}{\underset{\|}{C}}-CH=CH-CH_2-$ | H | — | H |
| H | — | H | $-CH_2-CH=CH-CO-NH-CH_2-$ | H | H | — |
| H | — | H | $-CH_2-CH=CH-CO-NH-CH_2-$ | — | H | H |
| H | — | H | $-CH_2-CH=CH-CO-NH-(CH_2)_2-NH-CO-NH-CH_2-$ | H | H | — |
| H | — | H | $-CH_2-CH=CH-CH_2-NH-CO-CH_2-CH_2-CO-NH-CH_2-$ | H | H | — |
| H | — | H | $-CH_2-CH=CH-CH_2-NH-CO-(CH_2)_3-CO-NH-CH_2-$ | — | H | H |
| H | — | H | $-CH_2-CH=CH-CO-NH-CH_2-CH_2-CH_2-$ | H | — | H |
| H | — | H | $-CH_2-CH=CH-CH_2-CO-NH-CH_2-$ | H | H | — |
| H | — | H | $-CH_2-CH=CH-CH_2-CO-NH-CH_2-$ | — | H | H |
| H | — | H | $-CH_2-CH=CH-CH_2-CO-NH-(CH_2)_4-NH-CO-NH-CH_2-$ | H | H | — |
| H | — | H | $-CH_2-CH=CH-CH_2-CO-NH-(CH_2)_6NH-CO-NH-CH_2-$ | — | H | H |
| H | — | H | $-CH_2-CH=CH-CH_2-NH-CO-NH-CH_2-$ | H | H | — |
| H | — | H | $-CH_2-CH=CH-CH_2-NH-CO-NH-CH_2-$ | — | H | H |
| H | — | H | $-CH_2-CH=CH-CH_2-NH-SO_2-NH-CH_2-$ | H | H | — |
| H | — | H | $-CH_2-CH=CH-CH_2-NH-SO_2-NH-CH_2-$ | — | H | H |
| H | — | H | $-CH_2-CH_2-CH_2-NH-CO-NH-CH_2-$ | H | H | — |
| H | — | H | $-CH_2-CH_2-CH_2-NH-CO-NH-CH_2-$ | — | H | H |
| H | — | H | $-CH_2-CH_2-CH_2-NH-SO_2-NH-CH_2-$ | H | H | — |
| H | — | H | $-CH_2-CH_2-CH_2-NH-SO_2-NH-CH_2-$ | — | H | H |
| H | — | H | $-CH_2-CH_2-CH_2-NH-CO-CH_2-CH_2-CO-NH-CH_2-$ | H | H | — |
| H | — | H | $-CH_2-CH_2-CH_2-NH-CO-CH_2-CH_2-CO-NH-CH_2-$ | — | H | H |
| H | — | H | $-CH_2-CH_2-CH_2-NH-CO-NH-(CH_2)_2-NH-CO-NH-CH_2-$ | H | H | — |
| H | — | H | $-CH_2CH_2CH_2-NHCONH-CH_2CH_2CH_2-$ | H | — | H |
| H | — | H | $-CH_2-CH_2-CH_2-NH-CO-NH-(CH_2)_3-NH-CO-NH-CH_2-$ | — | H | H |
| H | H | — | $-CH_2-NH-CO-NH-SO_2-NH-CH_2-$ | H | H | — |
| H | H | — | $-CH_2-NH-CO-NH-SO_2-NH-CH_2-$ | — | H | H |
| H | H | — | $-CH_2-NH-CO-NH-CO-NH-CH_2-$ | H | H | — |
| H | H | — | $-CH_2-NH-CO-NH-CO-NH-CH_2-$ | — | H | H |
| H | — | H | $-CH_2-(CH=CH)_2-CO-NH-CH_2-$ | H | H | — |
| H | — | H | $-CH_2-(CH=CH)_2-CO-NH-CH_2-$ | — | H | H |
| H | — | H | $-CH_2-(CH=CH)_2-CO-NH-CH_2-CH_2-CH_2-$ | H | — | H |
| H | — | H | $-CH_2-(CH=CH)_2-CO-NH-(CH_2)_2-NH-CO-NH-CH_2-$ | H | H | — |
| H | — | H | $-CH_2-(CH=CH)_2-CO-NH-(CH_2)_6-NH-CO-NH-CH_2-$ | — | H | H |

-continued

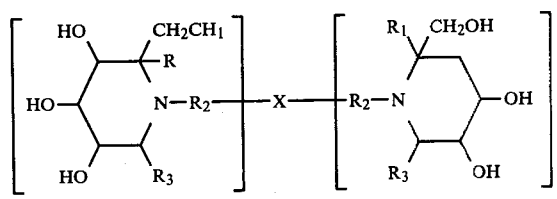

| R₁ | R₂ | R₃ | X | R₁' | R₂' | R₃' |
|---|---|---|---|---|---|---|
| H | — | CH₃ | —CH₂—NH—CO—NH—(CH₂)₆—NH—CO—NH—CH₂— | H | H | — |
| — | CH₃ | H | —CH₂—NH—CO—NH—(CH₂)₆—NH—CO—NH—CH₂— | — | H | H |
| H | CH₃ | — | —CH₂—NH—CO—(CH₂)₈—CO—NH—CH₂— | H | H | — |
| — | CH₃ | H | —CH₂—NH—CO—(CH₂)₈—CO—NH—CH₂— | — | H | H |
| H | H | — | —CH₂—NH—SO₂—⟨C₆H₄⟩—NH—CO—NH—CH₂— | — | H | H |
| H | CH₃ | — | —CH₂—NH—SO₂—⟨C₆H₄⟩—NH—CO—NH—CH₂— | — | H | H |
| H | H | — | —CH₂—NH—SO₂—⟨C₆H₄⟩—NH—CO—NH—CH₂— | — | CH₃ | H |
| H | H | — | —CH₂—NH—SO₂—⟨C₆H₄⟩—NH—CO—NH—CH₂— | H | H | — |
| H | H | — | —CH₂—NH—SO₂—⟨C₆H₄⟩—NH—CO—NH—CH₂— | — | H | H |
| — | H | H | —CH₂—NH—SO₂—⟨C₆H₄⟩—NH—CO—NH—CH₂ | H | H | — |
| H | H | — | —CH₂—NH—SO₂—⟨C₆H₄⟩—CH₂—NH—CO—NH—CH₂— | — | H | H |
| — | H | H | —CH₂—NH—SO₂—⟨C₆H₄⟩—CH₂—NH—CO—NH—CH₂— | H | H | — |
| H | CH₃ | — | —CH₂—NH—SO₂—⟨C₆H₄⟩—CH₂—NH—CO—NH—CH₂— | — | H | H |
| H | H | — | —CH₂—NH—SO₂—⟨C₆H₄⟩—CH₂—NH—CO—NH—CH₂— | — | CH₃ | H |
| H | — | H | —CH₂—(CH₂)₂—CH₂— | H | — | H |
| H | — | H | —CH₂—CH₂— | H | — | H |
| H | — | H | —CH₂—(CH₂)₅—CH₂— | H | — | H |
| H | — | H | —CH₂—CH₂—CH₂— | H | — | H |

-continued

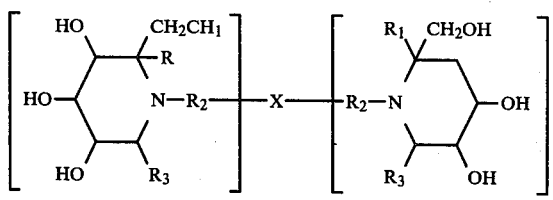

| R₁ | R₂ | R₃ | X | R₁' | R₂' | R₃' |
|---|---|---|---|---|---|---|
| H | — | H | —CH₂—(CH₂)₇—CH₂— | H | — | H |
| H | — | H | —CH₂—(CH₂)₈—CH₂— | H | — | H |
| H | — | H | —CH₂—⟨cyclohexane⟩—CH₂— | H | — | H |
| H | — | H | —(CH₂)₂—CO—O—CO—(CH₂)₂— | H | — | H |
| H | — | H | —CH(CH₃)—CH₂—CH₂—CO—O—CH₂—(CH₂)₄—CH₂— | H | — | H |
| H | — | H | —CH₂—⟨C₆H₄⟩—NH—CO—⟨C₆H₄⟩—CH₂— | H | — | H |
| H | — | H | —CH₂—CH(OH)—CH₂—O—CH₂—CH(OH)—CH₂— | H | — | H |
| H | — | H | —CH₂—(CH₂)₄—O—CO—NH—CH₂— | — | H | H |
| H | — | H | —CH₂—(CH₂)₄—O—CO—NH—CH₂— | — | CH₃ | H |
| H | — | H | —CH₂—(CH₂)₄—O—CO—NH—CH₂— | H | H | — |
| H | — | H | —CH₂—(CH₂)₉—O—CO—NH—CH₂— | — | H | H |
| H | — | H | —CH₂—(CH₂)₉—O—CO—NH—CH₂— | H | H | — |
| H | — | H | —CH₂—⟨C₆H₄⟩—CH=N—⟨C₆H₄⟩—SO₂—NH—CH₂— | — | H | H |
| H | — | H | —CH₂—⟨C₆H₄⟩—CH=N—⟨C₆H₄⟩—SO₂—NH—CH₂— | H | H | — |
| H | — | H | —CH₂—⟨C₆H₄⟩—CH=N—⟨C₆H₄⟩—CO—NH—CH₂— | H | H | — |
| H | — | H | —CH₂—⟨C₆H₄⟩—N=CH—⟨C₆H₄⟩—CO—NH—CH₂— | — | H | H |
| H | — | H | —CH(CH₃)—(CH₂)₂—CO—NH—(CH₂)₃— | H | — | H |
| H | — | H | —(CH₂)₆—NH—CO—(CH₂)₂— | H | — | H |
| H | — | H | —(CH₂)₅—CO—NH—CH₂— | — | H | H |
| H | — | H | —(CH₂)₅—CO—NH—CH₂— | H | H | — |
| H | — | H | —(CH₂)₃—NH—CO—NH—(CH₂)₆—NH—CO—NH—(CH₂)₃— | H | — | H |
| H | — | H | —(CH₂)₆—NH—CO—NH—(CH₂)₆—NH—CO—NH—(CH₂)₆— | H | — | H |
| H | — | H | —(CH₂)₆—NH—CS—NH—(CH₂)₆—NH—CS—NH—(CH₂)₆— | H | — | H |
| H | — | H | —(CH₂)₂—CO—NH—(CH₂)₆—NH—CO—(CH₂)₂— | H | — | H |

-continued $$\left[\begin{array}{c} HO \quad \overset{CH_2CH_1}{\underset{R}{|}} \\ HO \\ HO \quad \underset{R_3}{|} \end{array} N-R_2\right]-X-\left[R_2-N \begin{array}{c} \overset{R_1}{\underset{|}{}} CH_2OH \\ OH \\ \underset{R_3}{|} OH \end{array}\right]$$

| $R_1$ | $R_2$ | $R_3$ | X | $R_1'$ | $R_2'$ | $R_3'$ |
|---|---|---|---|---|---|---|
| H | — | H | $-(CH_2)_3-NH-CO-CH_2-\underset{}{\bigcirc}-NH-CO-(CH_2)_2-$ | H | — | H |
| H | — | H | $-CH_2-\underset{}{\bigcirc}-O-CO-NH-CH_2-$ | — | H | H |
| H | — | H | $-CH_2-\underset{}{\bigcirc}-O-CO-NH-CH_2-$ | H | H | — |
| H | — | H | $-CH_2-\underset{}{\bigcirc}\underset{O-CO-NH-CH_2-}{}$ | — | H | H |
| H | — | H | $-CH_2-\underset{}{\bigcirc}\underset{O-CO-NH-CH_2-}{}$ | H | H | — |
| H | — | H | $-CH_2-\underset{OCH_3}{\bigcirc}-O-CO-NH-CH_2-$ | — | H | H |
| H | — | H | $-CH_2-\underset{}{\bigcirc}-SO_2-NH-CH_2-$ | — | H | H |
| H | — | H | $-CH_2-\underset{}{\bigcirc}-SO_2-NH-CH_2-$ | H | H | — |
| H | — | H | $-(CH_2)_2-CO-NH-\underset{}{\bigcirc}-SO_2-NH-CH_2-$ | H | H | — |
| H | — | H | $-(CH_2)_6-NH-CO-NH-\underset{}{\bigcirc}-NH-CO-NH-(CH_2)_6-$ | H | — | H |
| H | — | H | $-(CH_2)_3-NH-CO-NH-\underset{}{\bigcirc}-NH-CO-NH-(CH_2)_3-$ | H | — | H |

-continued
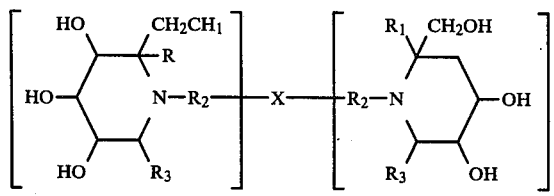
| $R_1$ | $R_2$ | $R_3$ | X | $R_1'$ | $R_2'$ | $R_3'$ |
|---|---|---|---|---|---|---|
| H | — | H | 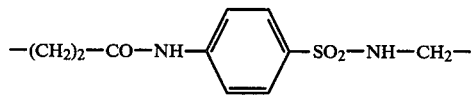 | — | H | H |
| H | — | H | 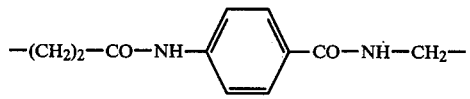 | — | H | H |
| H | — | H | 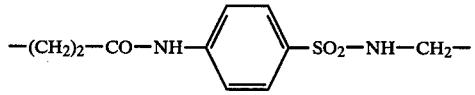 | H | H | — |
| H | — | H | 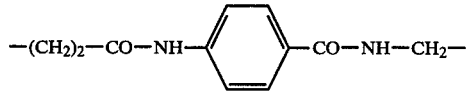 | H | H | — |
| H | — | H | 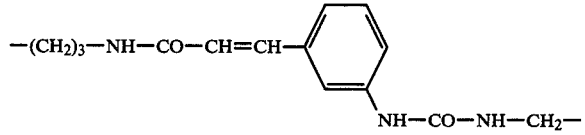 | — | H | H |
| H | — | H | $-CH_2-NH-CO-O-(CH_2)_4-O-CO-NH-CH_2-$ | — | H | H |
| H | — | H | $-CH_2-NH-CO-O-(CH_2)_5-O-CO-NH-CH_2-$ | — | H | H |
| — | H | H |  | — | H | H |
| — | H | H | 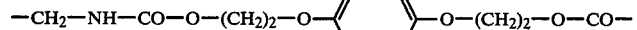<br> | — | H | H |
| — | H | H | 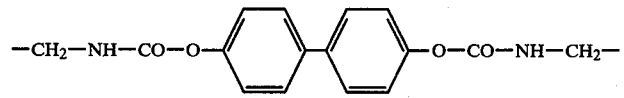 | — | H | H |
| H | H | — | 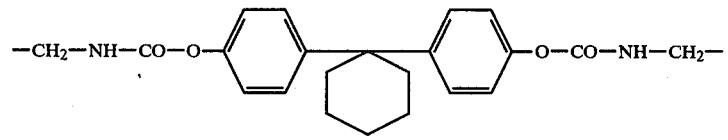 | H | H | — |
| — | H | H | 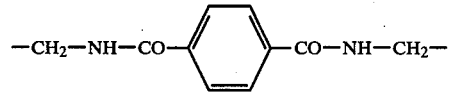 | — | H | H |

-continued

Structure: [HO, CH₂CH₁, HO, R, HO, N—R₂]—X—[R₂—N, R₁, CH₂OH, OH, R₃, OH] with substituents R, R₁, R₂, R₃ on the left cyclitol moiety and R₁', R₂', R₃' on the right.

| R₁ | R₂ | R₃ | X | R₁' | R₂' | R₃' |
|----|----|----|---|-----|-----|-----|
| H | H | — | —CH₂—NH—CO—(1,4-C₆H₄)—CO—NH—CH₂— | H | H | — |
| — | H | H | —CH₂—NH—CO—(C₆H₃, 2-Cl)—CO—NH—CH₂— | — | H | H |
| — | H | H | —CH₂—NH—CO—O—(1,4-C₆H₄)—CO—NH—CH₂— | — | H | H |
| — | H | H | —CH₂—NH—CO—O—(1,4-C₆H₄)—CO—NH—CH₂— | H | H | — |
| — | H | H | —CH₂—NH—CO—(C₆H₄)—O—(C₆H₄)—CO—NH—CH₂— | — | H | H |
| H | H | — | —CH₂—NH—CO—(C₆H₄)—CO—(C₆H₄)—CO—NH—CH₂— | H | H | — |
| — | H | H | —CH₂—NH—SO₂—(1,3-C₆H₄)—SO₂—NH—CH₂— | — | H | H |
| H | H | — | —CH₂—NH—SO₂—(1,3-C₆H₄)—SO₂—NH—CH₂— | H | H | — |
| — | H | H | —CH₂—NH—SO₂—(C₆H₄—C₆H₄)—SO₂—NH—CH₂— | — | H | H |
| H | H | — | —CH₂—NH—SO₂—(C₆H₄—C₆H₄)—SO₂—NH—CH₂— | H | H | — |
| H | H | — | —CH₂—NH—CO—O—(CH₂)₅—O—CO—NH—CH₂— | H | H | — |
| H | H | — | —CH₂—NH—CO—O—(CH₂)₄—O—CO—NH—CH₂— | H | H | — |
| — | H | H | —CH₂—NH—CO—O—(CH₂)₂—O—CO—NH—CH₂— | — | H | H |
| — | H | H | —CH₂—NH—CO—O—(CH₂)₂—O—(CH₂)₂O—(CH₂)₂—O—CO—NH—CH₂— | — | H | H |

-continued

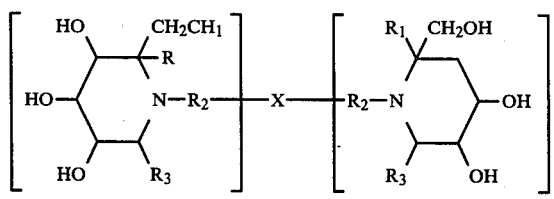

| R₁ | R₂ | R₃ | X | R₁' | R₂' | R₃' |
|---|---|---|---|---|---|---|
| H | H | — | —CH₂—NH—CO—O—(CH₂)₂—O—(CH₂)₂—O—CO—NH—CH₂— | H | H | — |
| — | H | H | —CH₂—NH—CO—O—CH₂—CH=CH—CH₂—O—CO—NH—CH₂— | — | H | H |
| — | H | H | —CH₂—NH—CO—O—CH₂—CH₂—CH₂—O—CO—NH—CH₂— | — | H | H |
| — | H | H | —CH₂—NH—CO—CH=CH—CO—NH—CH₂— | — | H | H |
| — | H | H | —CH₂—NH—CS—NH—(CH₂)₅—NH—CH₂— | — | H | H |
| — | H | H | —CH₂—NH—CO—O—⟨C₆H₄⟩—O—CO—NH—CH₂— | — | H | H |
| H | H | — | —CH₂—NH—COO—⟨C₆H₄⟩—O—CO—NH—CH₂— | H | H | — |
| — | H | H | —CH₂—NH—CO—NH—⟨C₆H₄⟩—O—⟨C₆H₄⟩—NH—CO—NH—CH₂— | — | H | H |
| H | H | — | —CH₂—NH—CO—NH—⟨C₆H₄⟩—S—⟨C₆H₄⟩—NH—CO—NH—CH₂— | H | H | — |
| — | H | H | —CH₂—NH—CO—NH—⟨C₆H₄⟩—S—⟨C₆H₄⟩—NH—CO—NH—CH₂— | — | H | H |
| — | H | H | —CH₂—NH—CO—HN—⟨C₆H₄⟩—SO₂—⟨C₆H₄⟩—NH—CO—NH—CH₂— | — | H | H |
| — | H | H | —CH₂—NH—CO—O—⟨C₆H₁₀⟩—O—CO—NH—CH₂— | — | H | H |
| — | H | H | —CH₂—NH—SO₂—⟨C₆H₄⟩—O—⟨C₆H₄⟩—SO₂—NH—CH₂— | — | H | H |
| — | H | H | —CH₂—NH—CO—NH—⟨C₆H₁₀⟩—NH—CO—NH—CH₂— | — | H | H |
| H | H | — | —CH₂—NH—CO—NH—⟨C₆H₉(CH₃)⟩—NH—CO—NH—CH₂ | H | H | — |

-continued

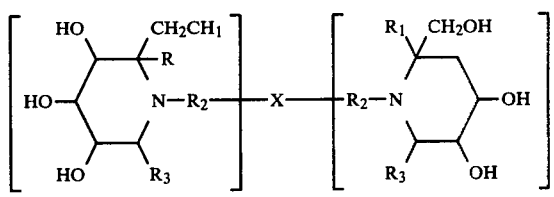

| R₁ | R₂ | R₃ | X | R₁' | R₂' | R₃' |
|---|---|---|---|---|---|---|
| — | H | H | -CH₂-NH-CO-NH-⟨cyclohexyl⟩-NH-CO-NH-CH₂- | — | H | H |
| — | H | H | -CH₂-NH-CO-NH-⟨cyclohexyl⟩-CH₂-⟨cyclohexyl⟩-NH-CO-NH-CH₂- | — | H | H |
| H | H | — | -CH₂-NH-CO-NH-⟨cyclohexyl⟩-CH₂-⟨cyclohexyl⟩-NH-CO-NH-CH₂- | H | H | — |
| — | H | H | -CH₂-NH-CO-NH-⟨p-phenylene⟩-NH-CO-NH-CH₂- | — | H | H |
| — | H | H | -CH₂-NH-CO-NH-⟨p-phenylene⟩-NH-CO-NH-CH₂- | H | H | — |
| H | H | — | -CH₂-NH-CO-NH-⟨p-phenylene⟩-NH-CO-NH-CH₂- | H | H | — |
| — | H | H | -CH₂-NH-CO-NH-⟨m-phenylene⟩-NH-CO-NH-CH₂- | — | H | H |
| — | H | H | -CH₂-NH-CO-NH-CH₂-⟨m-phenylene⟩-CH₂-NH-CO-NH-CH₂ | — | H | H |
| H | H | — | -CH₂-NH-CO-NH-CH₂-⟨m-phenylene⟩-CH₂-NH-CO-NH-CH₂- | H | H | — |
| — | H | H | -CH₂-NH-CO-NH-⟨biphenyl⟩-NH-CO-NH-CH₂- | — | H | H |

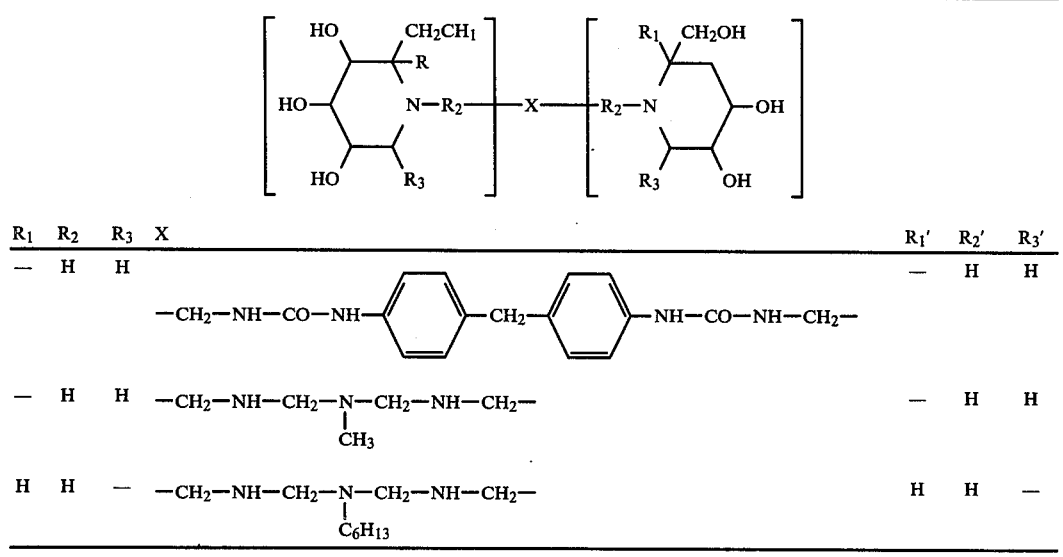

| $R_1$ | $R_2$ | $R_3$ | X | $R_1'$ | $R_2'$ | $R_3'$ |
|---|---|---|---|---|---|---|
| — | H | H | $-CH_2-NH-CO-NH-\text{C}_6\text{H}_4-CH_2-\text{C}_6\text{H}_4-NH-CO-NH-CH_2-$ | — | H | H |
| — | H | H | $-CH_2-NH-CH_2-N(CH_3)-CH_2-NH-CH_2-$ | — | H | H |
| H | H | — | $-CH_2-NH-CH_2-N(C_6H_{13})-CH_2-NH-CH_2-$ | H | H | — |

The following compounds can be obtained using appropriate reactants and the procedures specified above.

EXAMPLE 20

$N^1,N^4$-Bis[5-(1,5-Imino-1,5-didesoxy-D-glucityl)-methyl]-4,4'-oxy-bisphenylurea

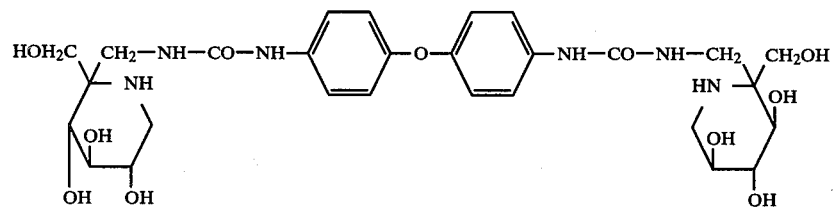

Rf value: 0.51
Rf value for 2-aminomethyl-2-hydroxymethyl-3,4,5-trihydroxypiperidine dihydrochloride=0.36.
Running agent: methanol/chloroform/25% strength ammonia in the volume ratio 3:2:2.

EXAMPLE 21

$N^1,N^4$-Bis-[5-(1,5-Imino-1,5-didesoxy-D-glucityl)-methyl]phenylene-1,4-bisurea

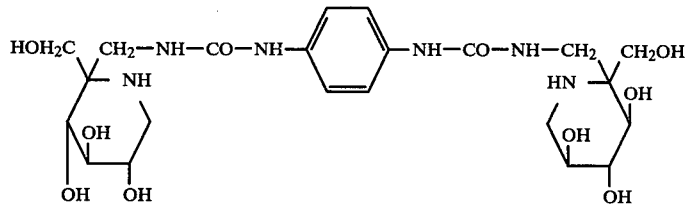

Rf value: 0.3
Comparison as for Example 20

EXAMPLE 22

N$^1$,N$^4$-Bis[5-(1,5-imino-1,5-didesoxy-D-glucityl)-methyl](4,6-dimethyl-phenylene-1,3-methylene-bisurea)

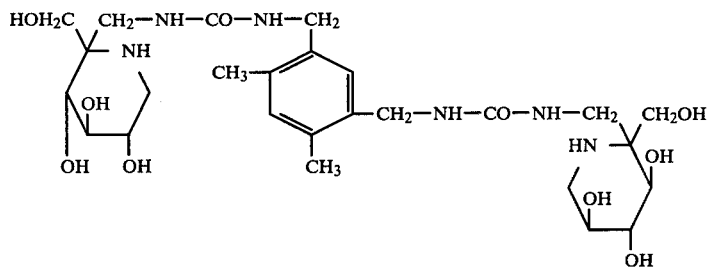

Rf=0.48

EXAMPLE 23

N$^1$,N$^4$-Bis[5-(1,5-imino-1,5-didesoxy-D-glucityl]diphenylmethane-4,4'-bisurea

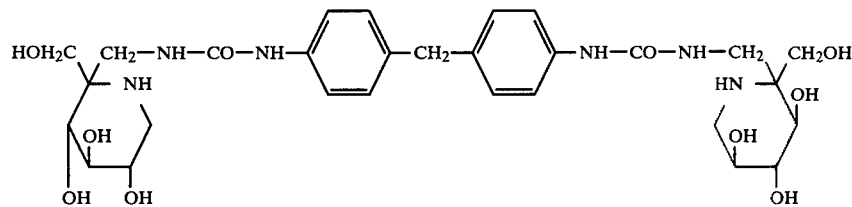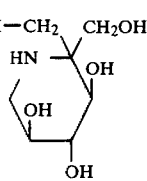

Rf value: 0.55
Comparison as for Example 20

EXAMPLE 24

N$^1$,N$^4$-Bis[1-α-(1,5-didesoxy-1,5-imino-D-glucityl)-methyl]-1,4-bisureido-cyclohexane

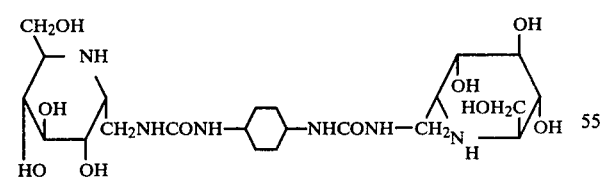

A $^{13}$C spectrum of the compound in D$_2$O was recorded (standard:

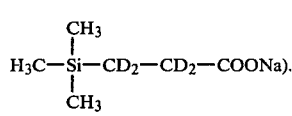

The 10 various C atoms of the compound absorb at (ppm, relative to the standard): 34.218, 38.503, 51.326, 57.040, 58.339, 64.670, 74.540, 74.865, 76.844 and 162.587.

EXAMPLE 25

N$^1$,N$^4$-Bis[1-α-(1,5-didesoxy-1,5-imino-D-glucityl)-methyl]-4,4'-bisureido-diphenylmethane

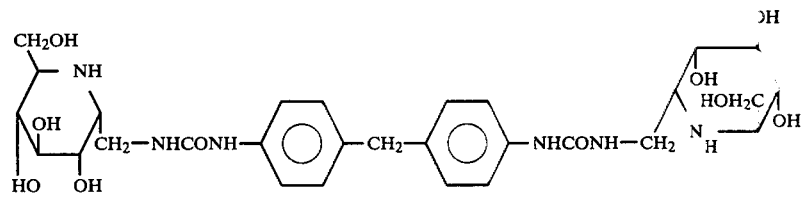

Melting point: 239° C.

EXAMPLE 26

N$^1$,N$^4$-bis[1-α-(1,5-didesoxy-1,5-imino-D-glucityl)-methyl]-1,3-phenylene-bisurea

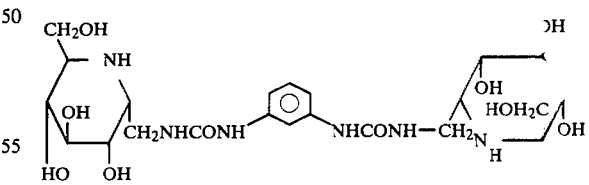

A $^{13}$C spectrum of the compound in D$_2$O was recorded (standard:

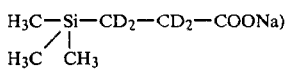

The 12 various C atoms of the compound absorb at (ppm, relative to the standard): 38.503, 57.073, 58.339, 64.670, 74.571, 74.896, 76.844, 155.478, 118.496, 132.360, 141.710 and 160.571.

EXAMPLE 27

N[1],N[4]-Bis[1-α-(1,5-didesoxy-1,5-imino-D-glucityl)-methyl]-α,α'-bisureido-m-xylene

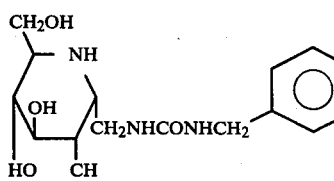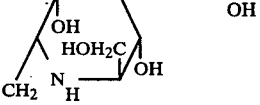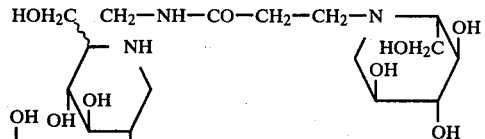

Rf value: 0.28; 1-aminomethyl-1-desoxynojirimicin: 0.23 (thin layer chromatography plates and running agent as in Example 2).

EXAMPLE 28

N[1],N[4]-Bis[1-α-(1,5-didesoxy-1,5-imino-D-glucityl)-methyl]-1,5-bisureido-naphthalene

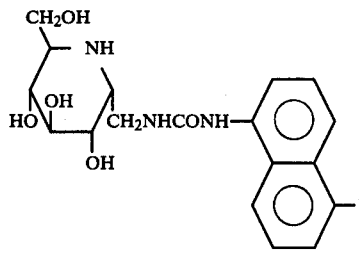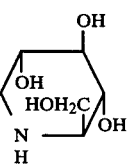

Melting point: 228° C.

EXAMPLE 29

N[1],N[4]-Bis-[1-α-(1,5-didesoxy-1,5-imino-D-glucityl)-methyl]-1,4-phenylene-bisurea

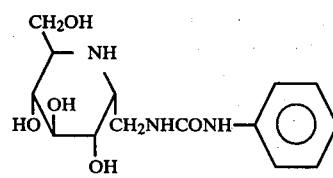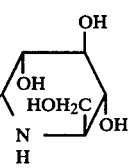

Rf value: 0.21; 1-aminomethyl-1-desoxynojirimicin: 0.23 (thin layer chromatography plates and running agent as in Example 2).

EXAMPLE 20

N-[(2-Hydroxymethyl-3,4,5-trihydroxy)-piperidine-2-methyl]-1-desoxynojirimicin-β-propionic acid amide is prepared analogously to Example 12, from 1-desoxynojirimicinyl-β-propionic acid and 2-aminomethyl-2-hydroxymethyl-3,4,5-trihydroxy-piperidine dihydrochloride.

The most important mass peaks are: m/e-247 (M-162); m/e=215; m/e=162 (M-247)

Rf value=0.29

Rf value of 2-aminomethyl-2-hydroxymethyl-3,4,5-trihydroxy-piperidine dihydrochloride=0.36.

Running agent: methanol/chloroform/25% strength ammonia in the volume ratio 3:2:2.

EXAMPLE 31

N,N'-{3-[(1',5'-didesoxy-1',5'-imino-D-glucit-yl)propionic acid]}-trimethylene-diamide

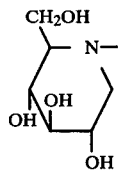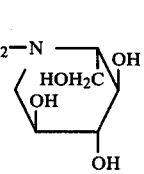

4.7 g of 1-desoxynojirimicinyl-β-propionic acid are stirred in 100 ml of absolute pyridine and 56 ml of water, with 0.86 ml of 1,3-diaminopropane and 6.24 g of dicyclohexylcarbodiimide, at 50° C. for 5 days. The mixture is cooled and filtered. The filtrate is concentrated, the residue is dissolved in water, the solution is filtered and the filtrate is concentrated again. The evaporation residue is dissolved in a little water and the product is purified over a cellulose column with aqueous acetone. 0.5 g of pure product is obtained in the form of a foam.
Rf value: 0.45.
Comparison as for Example 20

The following compound was prepared analogously:

EXAMPLE 32

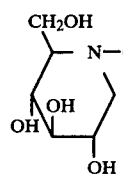

N,N'-[1-Desoxynojirimicinyl-(β-propionic acid])-p-phenylene-bisamide

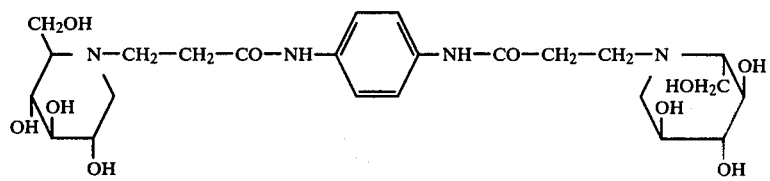

Rf value = 0.53
Comparison as for Example 20.

EXAMPLE 33

N,N'-Bis-[1,2(1,5-imino-1,5-didesoxy-D-glucit-yl)-methyl]benzene-1,3-disulphonamide dihydrochloride

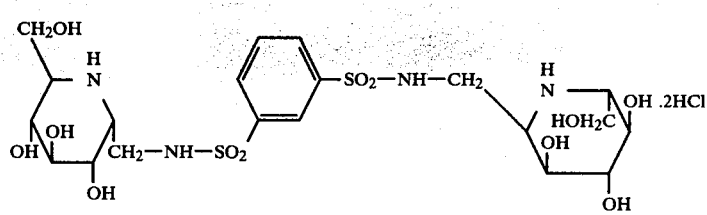

3 g of 1-aminomethyl-1-desoxynojirimicin are dissolved in a mixture of 30 ml of water and 90 ml of acetone and, after adding 2.1 ml of triethylamine, a solution of 2.04 g of benzene-1,3-disulphonic acid chloride in 30 ml of acetone is added dropwise. The mixture is stirred for 24 hours and concentrated, the residue is dissolved in about 1 liter of water and the anion exchanger Amberlite IRA 400 is added until the aqueous solution is free from chloride. The exchanger is filtered off and washed thoroughly with water. The exchanger is then stirred with 5% strength hydrochloric acid and filtered off. The filtrate is concentrated; the residue is dissolved in a little water and the product is purified over a cellulose column with aqueous acetone. The pure fractions are concentrated. The product crystallises on concentrating in the presence of isopropanol. 2.1 g of colourless crystals with a melting point from 118° C., with decomposition, are obtained.

EXAMPLE 34

N,N'-Bis[β-(N-1-desoxynojirimicinyl)-(ethyl-sulphonylethyl-)]-piperazine

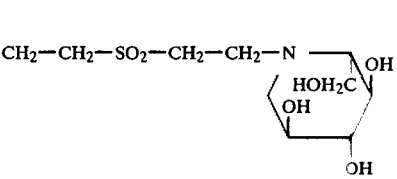

1.94 g of piperazine are dissolved in 15 ml of water, and a solution of 12.6 g of N-(vinylsulphonyethyl)-1-desoxynojirimicin (prepared from 1-desoxynojirimicin and divinyl sulphone, melting point: 156° C.) in 50 ml of water is added dropwise. The mixture is stirred for 18 hours and concentrated, the residue is dissolved in a little water and the product is purified over a cellulose column with aqueous acetone. The pure fractions are collected and concentrated. The evaporation residue is dissolved in warm methanol, the solution is filtered and the filtrate is concentrated, whereupon crystallisation starts. The residue is stirred with methanol and filtered off. 10.0 g of colourless crystals with a melting point from 175° C., with decomposition, are obtained.

EXAMPLE 35

N,N'-[3,3'-(1,4-Phenylene)-bis(2-propenyl)]-di(1-desoxy-nojirimicin)

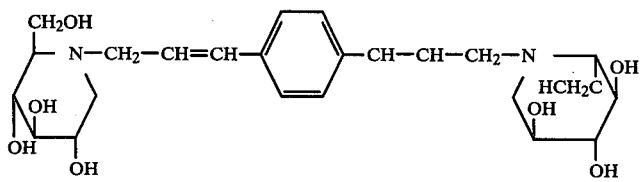

A solution of 9 g of β,β'-phenylene-di-acrolein in 270 ml of tetrahydrofurane is added to 14.1 g of 1-desoxynojirimicin in 425 ml of methanol and 29 ml of glacial acetic acid. The mixture is cooled to 0°–5° C. and 11.6 g of sodium cyanoborohydride are added in one operation. The mixture is stirred overnight at 20° C. and then concentrated. The evaporation residue is dissolved in 400 ml of methanol/water in the volume ratio 8:1 and the solution is discharged onto a column 30 cm long and 6 cm wide containing the cation exchanger Amberlite IR 200 (Serva). The column is washed thoroughly with methanol/water in the volume ratio 8:1 and then eluted with 2% strength ammonia. The fractions which contain the desired product are collected and concentrated. The crude product obtained is then purified over a cellulose column as described above. The product crystallises on concentrating in the presence of methanol. 4.1 g of colourless crystals of melting point 258°–260° C. are obtained, with decomposition.

EXAMPLE 36

The following compound was prepared analogously to Example 6, from 1-desoxynojirimicin and 1,4-dichlorobut-2-ine:

1,4[N,N'-Bis-(1,5-didesoxy-1',5'-imino-D-gluat)-yl]but-2-ine

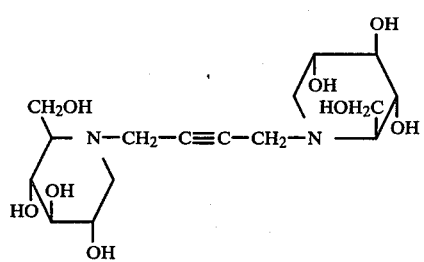

Melting point: 225° C. (decomposition)
Rf value: 0.25; 1-desoxynojirimicin: 0.42 (thin layer chromatography plates and running agent as in Example 2)

The following compounds are prepared analogously to Example 4.

EXAMPLE 37

N,N'-Bis-[5-(1,5-imino-1,5-didesoxy-D-glucityl)-methyl]fumaric acid-diamide.

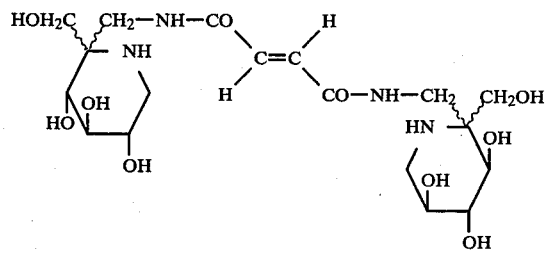

$R_f$ value: 0.19
$R_f$ value 2-aminomethyl-3,4,5-trihydroxy-piperidine dihydrochloride: 0,31 (thin layer chromatography plates and running agent as in Example 2).

EXAMPLE 38

N,N'-Bis-[5-(1,5-imino-1,5-didesoxy-D-glucityl)-methyl]-3-hexendicarboxylic acid diamide.

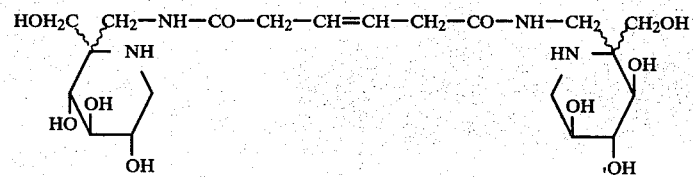

$R_f$ value: 0,23
The following compounds are prepared analogously to Example 9.

EXAMPLE 39

N¹,N⁴-Bis-[5-(1,5-didesoxy-1,5-imino-D-glucityl)-methyl]-1,5-bisureido-naphthalene.

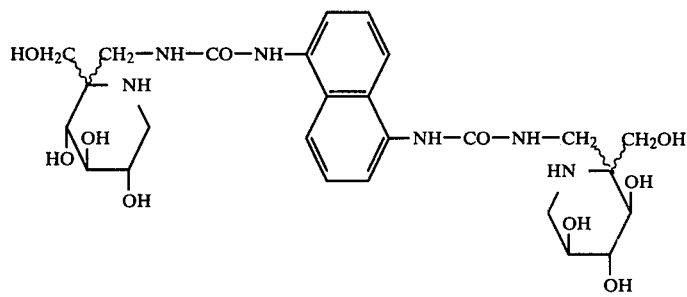

melting point: 232° C.
R$_f$ value 0,31

EXAMPLE 40

N¹,N⁴-Bis-[5-(1,5-didesoxy-1,5-imino-D-glucityl)-methyl]-4-phenoxy-1,3-phenylene-bisurea.

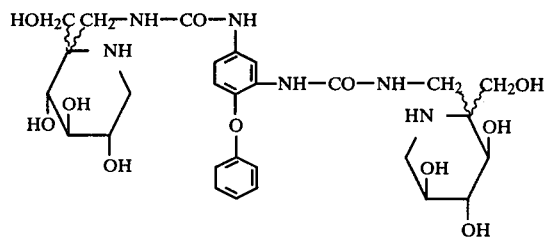

R$_f$ value 0,37

EXAMPLE 41

N¹,N⁴-Bis-[5-(1,5-didesoxy-1,5-imino-D-glucityl)-methyl]-1,4-bisureido-cyclohexane.

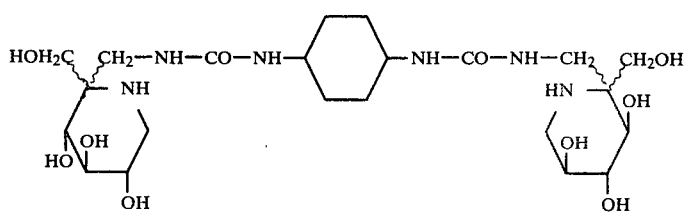

R$_f$ value: 0,30
This compound is prepared analogously to example 10 with 1,6-Dibromo-hexadiene-2,4 as starting material.

EXAMPLE 42

1,6[N,N'-Bis-(1',5'-didesoxy-1',5'-imino-D-glucit)-yl]hexadiene-2,4

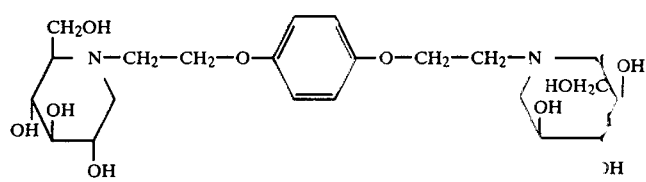

R$_f$ value: 0,48
R$_f$ value for 1-desoxynojirimycin: 0,53

EXAMPLE 43

1,4-Bis{2[N-1',5'-didesoxy-1',5'-imino-D-glucit)-yl]ethoxy}-benzene 2,95 g of 1-Desoxynojirimycin were stirred at 100° C. for 5 hours in 25 ml absolute DMF with 5 g of potash and 2,9 g Bis(2-bromoethoxy)-benzene. The hot solution was suction-filtered and the solvent was removed from the filtrate. The residue was dissolved in a small amount of methanol/water and purified over a cellulose/acetone column. After recrystallization from water 1,1 g of colorless crystals having a melting point of 226°-228° C. were obtained.
Analogously were produced:

EXAMPLE 44

4,4'-Bis{2[N-(1',5'-didesoxy-1',5'-imino-D-glucit)-yl]ethoxy}-diphenyl

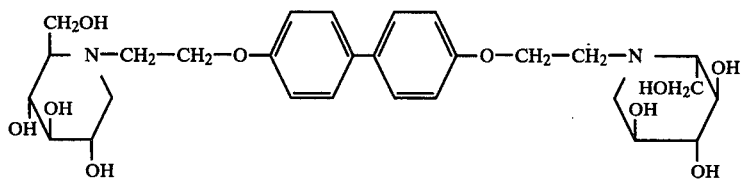

m.p. 238° C. (decomp.)

EXAMPLE 45

4,4'-Bis{2[N-(1',5'-didesoxy-1',5'-imino-D-glucit)-yl]ethoxy}-benzoesäurebenzylamid

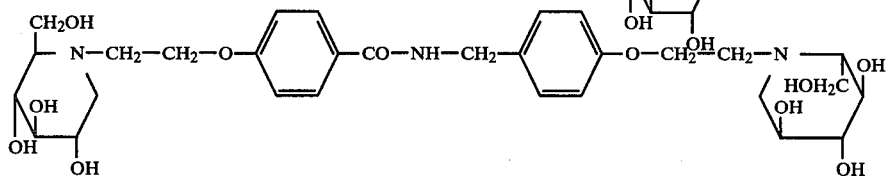

$R_f$-value 0.68; $R_f$ value of of Desoxynojirimycin=0.54 (running agent methanol/chloroform/ammonia 25% 3:2:2).

EXAMPLE 46

N-{4[2-N'-<1',5'-didesoxy-1',5'-imino-D-glucit>-yl)ethoxy]-benzyl}-1-desoxynojirimycin

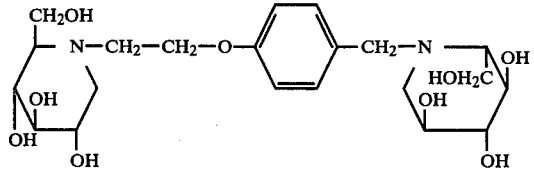

This compound was obtained through reaction of 4-(β-bromoethoxy)-benzaldehyde with 1-desoxynojirimycin in the way described in Example 35 to yield N-{4[β-bromoethoxy]benzyl}-1-desoxynojirimycin and subsequent reaction with 1-desoxynojirimycin under the conditions set forth in Example 43.
m.p. 155° C. (decomp.)

EXAMPLE 47

1-{4-[2(N<1',5'-didesoxy-1',5'-imino-D-glucit>-yl)ethoxy]-benzamidomethyl}-1-desoxynojirimycin

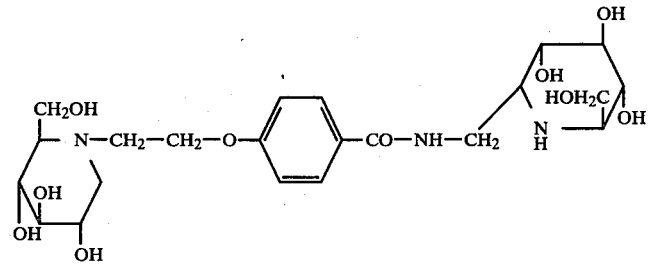

$R_f$-value 0.45 (running agent as in Example 45)

EXAMPLE 48

5-{4-[2(N<1',5'-didesoxy-1',5'-imino-D-glucit>-yl)ethoxy]-benzamidomethyl}-1-desoxynojirimycin

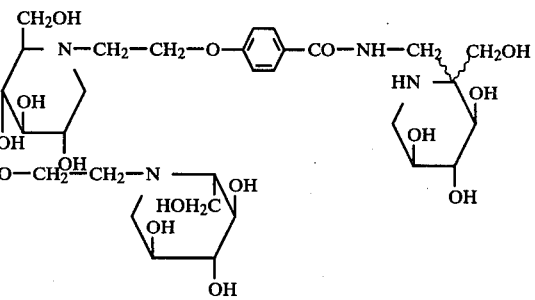

$R_f$-value 0.47 (running agent as in Example 45)

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to a warm-blooded animal is converted in the patient's body to the active compound.

What is claimed is:

1. A compound of the formula

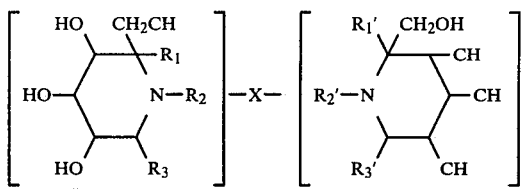

in which
R₁, R₁', R₃ and R₃' denote a hydrogen atom or a direct bond to X,
R₂ and R₂' denote a hydrogen atom, a $C_1$ to $C_4$ alkyl group or a direct bond to X, with the proviso that one and only one of the radicals R₁, R₂ and R₃ and one and only one of the radicals R₁', R₂' and R₃' represent a direct bond to X, and
in which
X corresponds to the formula $$-(A)_m-(R_4)_n-(Y)_p-(R_5)_q-(B)_r-$$

in which
A and B independently denote, $CH_2$, $CH_2-NH$, $CH_2-NH-CO$, $CH_2-NHCONH$, $CH_2-NH-SO_2NH$, $CH_2-NH-SO_2$, $CH_2-NHCS-NH$, $CH_2-NH-COO$, $CH_2-NHCS$,

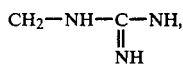

$CH_2-O$, CO or COO,
R₄ and R₅ independently correspond to the formula $$-(R_{13})_s-(U)_t-(R_{14})_v-$$

in which
R₁₃ and R₁₄ independently denote $C_1$ to $C_{18}$-alkylidene, $C_2$ to $C_{18}$-alkenylidene with up to three double bonds, $C_2$ to $C_{10}$ alkenylidene, $C_3$-$C_{10}$-cycloalkylidene
phenylene, phenylene with one or two substituents from phenoxy, $C_1$ to $C_4$ alkyl,
F, Cl, or Br or piperazine,
U denotes O, S, SO, $SO_2$, NH, $NR_6$, CO, COO, CS, OCOO, NHCOO, CONH, NHCONH, NHCSNH, CH=N, $SO_2NH$ or $NHSO_2NH$,
and
s, t, v, independently are 0 or 1,
Y has the meaning given for U, or has any of the meanings given for R₁₃ and R₁₄, and
m, n, p, q and r are 0 or 1, with the proviso that the sum of m and r is 1 or 2 and that p is 0 when n and/or q are 0 and with the proviso that there are excluded the compounds of the formula

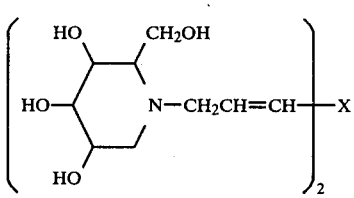

wherein X is phenylene.

2. A compound according to claim 1, in which X is $(CH_2)-C=C-(CH_2)_a$ wherein a is an integer from 1 to 6.

3. A compound according to claim 1, in which X is $-(CH_2)_b-$ wherein b is an integer from 1 to 6.

4. A compound according to claim 1, having the formula

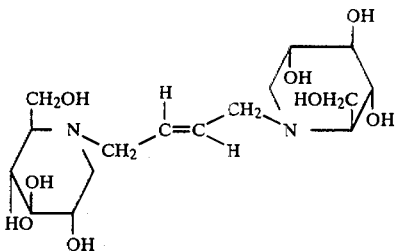

5. A compound according to claim 1, having the formula

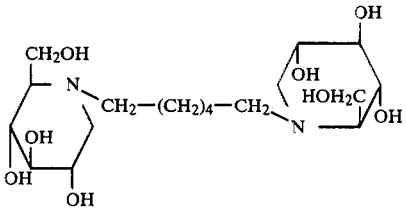

6. A compound according to claim 1, having the formula

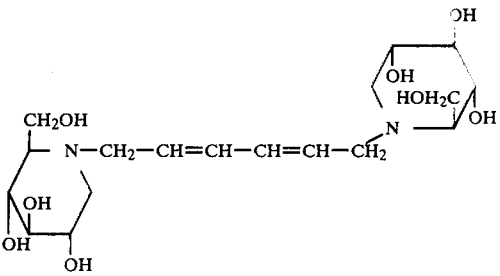

7. A compound according to claim 1, in which A denotes $CH_2$ if X is linked via R₂, or $CH_2-NHCO$, $CH_2NHSO_2$, $CH_2NHCOO$, $-CH_2NHCSNH-$ or $CH_2-NHCONH$ if X is linked via R₁ or R₃, B denotes $CH_2$ if X is linked via R₂', or $CH_2NHCO$, $CH_2NHSO_2$, $CH_2NHCOO$, $-CH_2NHCSNH-$ or $CH_2NHCONH$ if X is linked via R₁' or R₃', R₁₃ and R₁₄ denote $C_1$ to $C_{18}$-alkylidene, $C_2$ to $C_{18}$-alkenylidene or phenylene, U denotes O, $SO_2$, CO, $CH_2$, S, SO, NH, CONH, NHCONH, NHCSNH, $SO_2NH$, Y is U or CH=CH, phenylene or phenylene with one or two substitutents from $C_1$ to $C_4$ alkyl, F, Cl, or Br, m and n denote 1, and r, p and q denote 0 or 1.

8. A compound according to claim 1, in which
A denotes $CH_2$ if X is linked via R₂, or $CH_2-NHCO$, $CH_2NHSO_2$, $CH_2NHCOO$ or $CH_2NHCONH$ if X is linked via R₁ or R₃ and
B denotes $CH_2$ if X is linked via R₂' or $CH_2NHCO$, $CH_2NHSO_2$, $CH_2NHCOO$ or $CH_2NHONH$ if X is linked via R₁' or R₃'.

9. A pharmaceutical composition containing as an active ingredient an effective amount for combating diabetes, hyperlipamia or adiposity, of a compound according to claim 1 in admixture with a solid, liquid or liquefied gaseous diluent.

10. A pharmaceutical composition of claim 9 in the form of a sterile or physiologically isotonic aqueous solution.

11. A composition according to claim 9 or 10 containing from 0.5 to 99.5% by weight of the said active ingredient.

12. A medicament in dosage unit form comprising an effective amount for combating diabetes, hyperlipemia or adiposity, of a compound of claim 1 together with an inert pharmaceutical carrier.

13. A medicament of claim 12 in the form of tablets, pills, dragees, capsules, ampoules or suppositories.

14. A method of combating diabetes, hyperlipemia or adiposity which comprises administering to the animals an effective amount for combating diabetes, hyperlipemia or adiposity, of active compound according to claim 1 either alone or in admixture with a diluent or in the form of a medicament.

15. A method of combating adiposity, diabetes or hyperlipaemia in warm-blooded animals which comprises administering to the animals an effective amount for combating adiposity, diabetes or hyperlipaemia, of active compound according to claim 1 either alone or in admixture with a diluent or in the form of a medicament.

16. A method according to claim 14 or 15 in which the active compound is administered in an amount of 1 to $1 \times 10^4$ saccharase inhibitor units per kg body weight per day.

17. A medicament feed comprising an effective amount of a compound according to claim 1 and a nutritious material.

* * * * *